United States Patent
Zhu et al.

(10) Patent No.: US 11,117,932 B2
(45) Date of Patent: Sep. 14, 2021

(54) PEPTIDES FOR SPECIFIC INHIBITION OF JAG 1-NOTCH 1 PATHWAY

(71) Applicants: The Hong Kong Polytechnic University, Hong Kong (CN); The Royal Institution for the Advancement of Learning/McGill University, Montreal (CA)

(72) Inventors: Xuezhen Zhu, Hong Kong (CN); Yu-Wai Chen, Hong Kong (CN); Tak Hang William Chan, Hong Kong (CN); Ming Cheung Chow, Hong Kong (CN)

(73) Assignees: The Hong Kong Polytechnic University, Hong Kong (CN); The Royal Institution for the Advancement of Learning/McGill University, Montreal (CA)

( * ) Notice: Subject to any disclaimer, the term of this patent is extended or adjusted under 35 U.S.C. 154(b) by 0 days.

(21) Appl. No.: 17/261,573

(22) PCT Filed: Jul. 19, 2019

(86) PCT No.: PCT/IB2019/056215
§ 371 (c)(1),
(2) Date: Jan. 20, 2021

(87) PCT Pub. No.: WO2020/016855
PCT Pub. Date: Jan. 23, 2020

(65) Prior Publication Data
US 2021/0246168 A1 Aug. 12, 2021

Related U.S. Application Data

(60) Provisional application No. 62/700,957, filed on Jul. 20, 2018.

(51) Int. Cl.
C07K 7/08 (2006.01)
C07K 7/06 (2006.01)
A61K 45/06 (2006.01)
A61K 31/7004 (2006.01)
A61K 38/00 (2006.01)

(52) U.S. Cl.
CPC ............ C07K 7/08 (2013.01); A61K 31/7004 (2013.01); A61K 45/06 (2013.01); C07K 7/06 (2013.01); A61K 38/00 (2013.01)

(58) Field of Classification Search
None
See application file for complete search history.

(56) References Cited

PUBLICATIONS

Funahashi et al. "A Notch1 Ectodomain Construct Inhibits Endothelial Notch Signaling, Tumor Growth, and Angiogenesis" Cancer Research 68:4727-4735. (Year: 2008).*

* cited by examiner

*Primary Examiner* — Sudhakar Katakam
*Assistant Examiner* — Zachary J Miknis
(74) *Attorney, Agent, or Firm* — Law Offices of Albert Wai-Kit Chan, PLLC

(57) ABSTRACT

Aberrant cross talk between Notch ligand (e.g. Jag1) and Notch receptor (e.g. Notch1) has been implicated in tumorigenesis in the colon. Inhibition of Notch pathway is therefore an attractive approach for treating diseases with upregulated Jag1 e.g. colorectal cancer (CRC). Pan-notch inhibitors like gamma secretase inhibitors (GSIs) have been developed to inhibit Notch and its downstream events. However, severe gastrointestinal toxicity profiles impede the clinical development of GSIs. The present invention develops novel oligopeptides that specifically inhibit Jag1-Notch1 pathway without interfering DLL1-Notch1 or DLL4-Notch1, which demonstrates a clear advantage over pan-notch inhibitors.

15 Claims, 16 Drawing Sheets

Specification includes a Sequence Listing.

HCT-15

PEPTIDES FOR SPECIFIC INHIBITION OF JAG 1-NOTCH 1 PATHWAY

FIELD OF THE INVENTION

The present disclosure relates to Jag1-Notch1 pathway inhibitors.

BACKGROUND OF THE INVENTION

Notch signaling pathway is an evolutionarily-conserved process that contributes to development of multiple tissues and organs. Notch signalling involves a cell-cell communication process which requires binding of a membrane-tethered Notch ligand from the signal-sending cell to a transmembrane Notch receptor on a juxtaposed signal-receiving cell. There are 5 mammalian Notch ligands (Delta-like: DLLL. DLL3, DLL4 and Jagged: Jag1. Jag2) and four Notch receptors (Notch1 to 4). Notch receptors are single-pass transmembrane proteins. The extracellular domain consists of 29 to 36 EGF-like repeats followed by a negative regulatory region (NRR). Formation of ligand-receptor binary complex induces a series of proteolytic events including the last step of gamma secretase-dependent cleavage that liberates Notch intracellular domain (NICD). NICD will translocate into the nucleus, interacts with DNA-binding protein CSL/CBF1 and Mastermind-like protein (MAML) to induce transcription of downstream target genes including Hes1 and Hey1.

Dysregulation of Notch pathway is associated with various anomalies and disorders including CADASIL syndrome. Alagille syndrome and cancers. Oncogenic role of Notch was first identified in human T-ALL where a chromosomal translocation produced a constitutively-active NICD [1].

Notch signaling regulates tumorigenesis of colorectal cancer by regulating apoptosis, angiogenesis, cell migration and proliferation. Upregulation of Notch1 and Notch4 in cancer stem cells has been observed. Jag1 seems to be the main Notch ligand in driving the Notch signaling in cancer stem cells. Notch1 and its target Hes1 are associated with tumor grade [2] and Hes1 is overexpressed in primary colon cancer tissues [3]. Silencing of Jag1 inhibits colorectal cancer growth [4]. Notch1 and Jag1 are co-upregulated in human colon adenocarcinoma [5]. It has been proposed that Jag1 is the link between Wnt and Notch pathways in colon cancer [6].

Various strategies have been explored to inhibit Notch signaling for therapeutic purposes. Inhibition of proteolytic cleavage and activation of Notch receptor is one important class of Notch inhibitors. First, targeting the furin convertase-dependent site 1 (S1) cleavage of Notch receptor was unsuccessful in D. melanogaster [7]. Besides, Furin convertase has other target proteins including TGFβ, insulin receptor, adhesion molecules and matrix metalloproteinases. Inhibition of Furin convertase may have the risk of off-target effects. Second, targeting the metalloproteinase ADAM10- or ADAM17-dependent site 2 (S2) cleavage of Notch receptor may also have the risk of off-target effects because ADAMS are also involved in processing of tumor necrosis factor (TNF) and the interleukin-6 receptor (IL-6R). Third, targeting γ-secretase-dependent S3 cleavage of Notch receptor has been proven to be very effective in inhibiting all Notch receptors [8, 9].

The use of γ-secretase inhibitors (GSIs) in inhibiting Notch pathway in treating cancers has been extensively investigated. They have been combined with anticancer drugs in several clinical trials. While GSIs are highly effective in inhibiting Notch pathway, they are not specific for individual Notch pathway, i.e. they are pan-Notch inhibitors. Besides inhibiting Notch signaling, GSIs can also indiscriminately block other signaling pathways downstream of gamma-secretase. This non-specific inhibition of both Notch and non-Notch pathways results in severe gastrointestinal toxicity found in both animals and humans in clinical trials, resulting in goblet cell metaplasia of intestinal stem cells [10]. At this point, there is no GSIs that can specifically target individual Notch pathway. The possibility of reducing GI toxicity by specifically inhibiting Notch pathway was demonstrated using a Notch1 or Notch2 specific neutralizing antibody [11, 12].

Notch signaling can also be inhibited after NICD has been translocated to nucleus, by disrupting CSL-NICD-MAML transcriptional complex. Stapled peptides targeting the complex formation was effective in treating T-ALL in laboratory animals [13]. Although the stapled peptides show promising effects in a relevant murine model of T-ALL, the potential of the stapled peptides as a therapeutic agent still need to be fully evaluated. In case of inhibiting CSL-NICD-MAML complex formation, the stapled peptides must overcome the plasma membrane and nuclear membrane barrier. Besides stapled peptides, small molecule targeting tertiary transcription complex has also been reported [14].

Interaction between EGF repeats 1 and 12 of Notch receptor and DSL and MNNL domains on Notch ligands, respectively, are critical in Notch signaling. Co-crystal structures of DLL4-Notch1 [15] and Jag1-Notch1 extracellular domains [16] illustrated the importance of the above interaction. In 2017, Lucca et al [16] solved the co-crystal structure of binary complex containing part of the extracellular domain of Notch (EGF-like repeats 8-12; shown in FIG. 1) and part of the extracellular domain of Jag1 (MNNL, DSL, and EGF-like repeats 1-3; shown in FIG. 1). The interaction is via an antiparallel contact interface between Notch1 and Jag1 extracellular domains extending 120 Å in length. The interface includes two discrete sites of interaction, with site 1 covering EGF repeats 11-12 of Notch1 and MNNL-DSL domains of Jag1, and the site 2 from EGF repeats 8-10 of Notch1 and EGF repeats 1-3 of Jag1. The complex also revealed the crucial interaction of an O-linked fucose at T467 in EGF repeat 12 of Notch1.

Modulation of extracellular ligand-receptor interaction is a promising strategy to target Notch signaling. Antibodies targeting EGF repeats 11-12 of the Notch1 and Notch2 receptors can block ligand-receptor interaction and reduce Notch signaling [17]. In terms of targeting Notch ligands. Dll4 antibodies have shown great promise for inhibiting angiogenesis [18] although serious toxicity issues were reported in clinical studies [19, 20]. Neutralizing antibodies that can target Notch1 or Notch2 NRR regions specifically were also effective in inhibiting Notch signaling. Due to their specific inhibition of only 1 type of Notch receptors, these specific Notch antibodies have a clear advantage over pan-Notch inhibitors, such as GSIs, in reducing gastrointestinal (GI) toxicity issues [21]. Jag1 is a promising therapeutic target in Notch signaling [22], however, strategy targeting Jag1 interaction is still limited. On top of colorectal cancer described above, Jag1-Notch1 inhibitors are expected to be effective in other lymphoma and glioblastoma where Jag1 is frequently upregulated [23].

SUMMARY OF THE INVENTION

Accordingly, it is the object of the present disclosure to provide a novel ligand- or receptor-specific agents to target Jag1-Notch1 interactions, taking advantage of the latest X-ray structure of Jag1-Notch1 binary complex [16].

Oligopeptides that specifically inhibit Jag1-Notch1 pathway without interfering DLL1-Notch1 or DLL4-Notch1 are generated. As dual inhibition of Notch1 and Notch2 causes intestinal toxicity, selective inhibition of Notch1 by the peptides demonstrates a clear advantage over pan-notch inhibitors. The most potent peptide inhibited proliferation of colon cancer S1-M1-80 cells with the half maximal inhibitory concentration ($IC_{50}$) in the sub-micromolar level. Blockade of Jag1-Notch1 significantly suppresses proliferation of human colon cancer cells in clonogenic assay in vitro. Mechanistically, the concerned peptides bind directly to Notch ligand Jagged1 to block Jag1-Notch1 interactions.

Those skilled in the art will appreciate that the disclosure described herein is susceptible to variations and modifications other than those specifically described.

Other aspects and advantages of the disclosure will be apparent to those skilled in the art from a review of the ensuing description.

The above and other objects and features of the present disclosure will become apparent from the following description of the disclosure, when taken in conjunction with the accompanying drawings.

DETAILED DESCRIPTION OF THE INVENTION

The present invention is not to be limited in scope by any of the specific embodiments described herein. The following embodiments are presented for exemplification only.

Results

Designing Jag1-Notch1 Disrupting Peptides

Figure 1A:
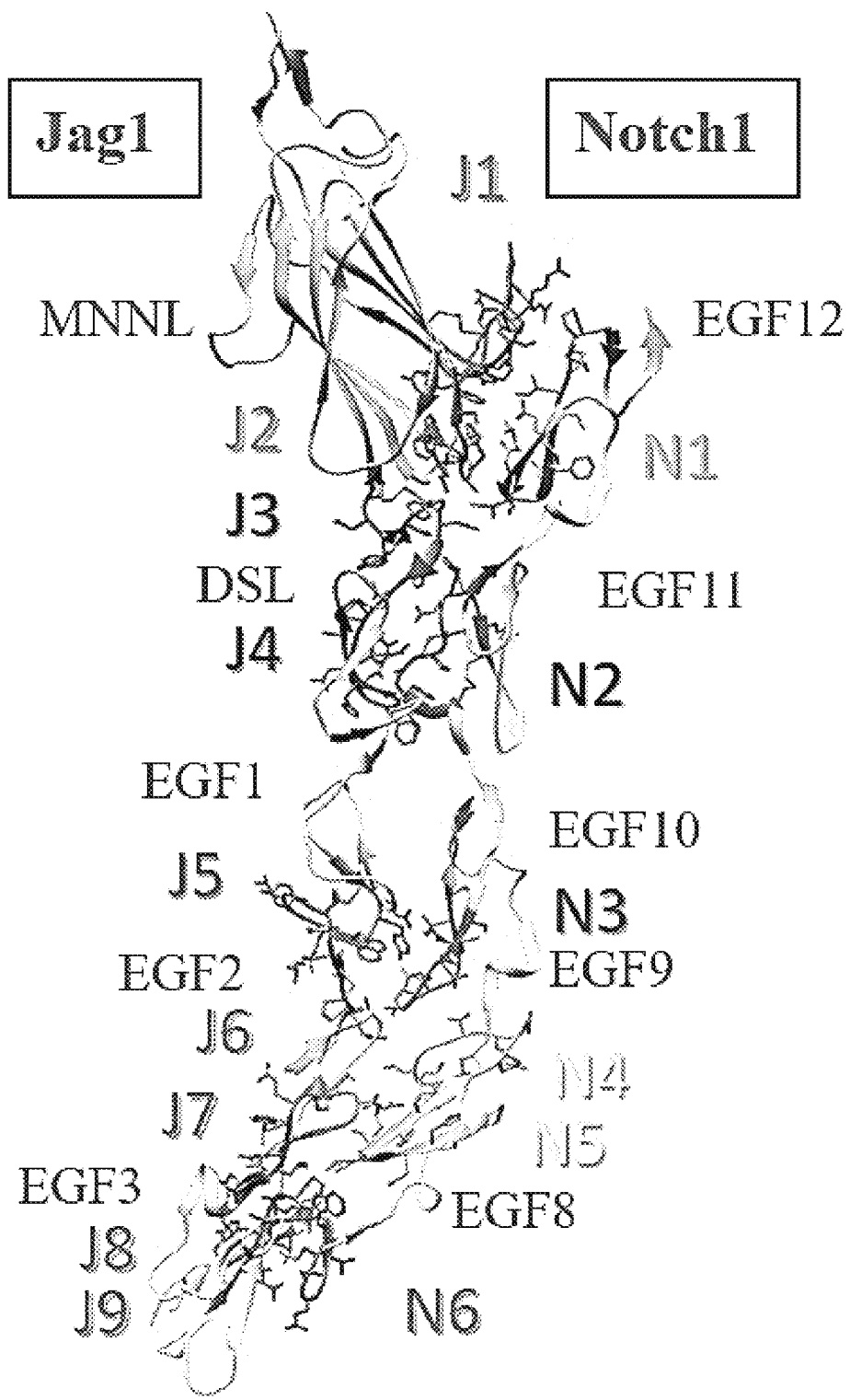
FIG. 1 shows design of peptides. (A). Co-crystal structure of the binary complex of part of the extracellular domains of Jag1 and Notch1 adopted from [16]. Peptides used to disrupt Jag1-Notch1 interaction are highlighted where J1 to J9 (SEQ ID NO: 1 to 9) are derived from Jag1 and N1 to N6 (SEQ ID NO. 10 to 15) are derived from Notch1. (B). Interaction of peptide N1 (SEQ ID NO: 10) with MNNL of Jag1 via L468, D469.1477 and P480. N1 (SEQ ID NO: 10) peptide (C467-G481 of Notch) is shown here with the 4 residues within 3 angstrom of MNNL domain of Jag1. L468 interacts with F126, P129 and F94 of Jag1; D469 interacts with A127 of Jag1. 1477 interacts with S93. E81 and F94 of Jag1; P480 interacts with R87 of Jag1. (C). Interaction of the 4 important residues of L468. D469, 1477 and P480 on EGF like repeat 12 of Notch with the corresponding residues in MNNL domain of Jag1. Distance between the 5 important residues with their partners in MNNL are shown (P480: 3.7 Å; 477: 3.5 Å, 3.1 Å, 3.8 Å, 3.8 Å; L468: 3.9 Å, 4.0 Å, 4.0 Å, 4.1 Å; D469: 4.0 Å). These residues will be mutated with the objective of achieving closer proximity to their interacting residues in Jag1. (D). Schematic diagram of cellular co-culture assay for study Notch ligand-receptor interaction in vitro.

In mammals, there are 5 Notch ligands (Jag1, Jag2, DLL1. DLL3 and DLL4) and 4 Notch receptors (Notch 1 to 4). Ligand-receptor interaction involves several EGF-like repeats in the extracellular regions. The molecular details of ligand-receptor interaction help us to design new inhibitors for targeting ligand-receptor interaction. Detailed interaction was revealed in two recent co-crystal structures of ligand-receptor binary complex in 2017 (Jag1-Notch1). The structure revealed the molecular details of the critical interaction between EGF-like repeat 12 and O-linked fucose at T466 of Notch1 and MNNL domain of Jag1 (FIG. 1A).

Since Jag1-Notch interaction takes place at sites S1 and S2 according to co-crystal structure, the reason is that peptides derived from these interacting sites could work as a 'decoy' and block the Jag1-Notch1 interactions. Notch1-derived decoy peptide has been used to disrupt Notch ligand DLL4, thereby inhibiting morphogenesis of endothelial cells expressing Notch4 [24]. Soluble Jag1 peptide can inhibit Jag1-mediated Notch signalling; inhibiting the downstream CSL-dependent transcription [25]. It is hypothesized that peptides designed from Jag1 or Notch1 side will be more potent and specific in disrupting the interactions.

Nine peptides are designed from Jag [(J1 to J9 (SEQ ID NO: 1 to 9)] and six peptides from Notch1 [(N1 to N6 (SEQ ID NO: 10 to 15)]. Their positions in Jag1 and Notch 1 are shown in FIG. 1A and their corresponding peptide sequence are shown in Table 1. Focus have been on the contact residues at the interacting sites S1 and S2. For instance, five residues on EGF repeat 12 of Notch1 (L468, D469, Q470, I477, P480) make contacts with various residues with MNNL of Jag1. Therefore a linear peptide N1 (SEQ ID NO: 10) (C467 to G481 of EGF repeat 12 of Notch) which encompasses the above interacting residues (FIGS. 1B and C) are designed. Such approach is used to generate two groups of peptides from either Jag1 [(J1-J9 (SEQ ID NO: 1 to 9)] or from Notch1 [N1-N6 (SEQ ID NO: 10 to 15)]. In case the interacting region involves a cysteine S—S disulphide bond, the peptide designed will also have a S—S disulphide bond in it.

Figure 2A:
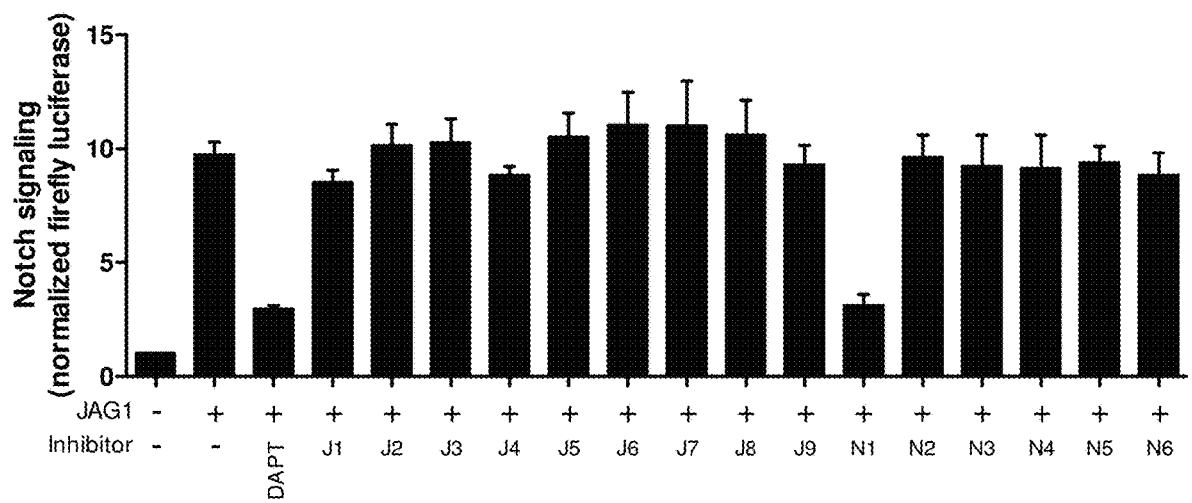
FIG. 2 shows screening of peptides. (A). Co-culture assays of Notch1 signalling, induced with Jag1 expressing cells (+Jag1). −Jag1, control for no induction; DAPT 50 µM in DMSO; Peptides [J1 to J9 (SEQ ID NO: 1 to 9) and N1 to N6 (SEQ ID NO: 10 to 15)], 100 µM in $H_2O$; Values represent Notch reporter gene expression relative to control reporter, normalized to the −Jag1 values. Peptides (100 µM) are tested for their cytotoxicity toward human colon cancer cell lines HCT-116 (B) and HCT-15 (C) and their ability to downregulate NICD1 in HCT-116 (D) and HCT-15 (E). Cells treated with γ-secretase inhibitor DAPT were used as positive control.
Figure 2B:
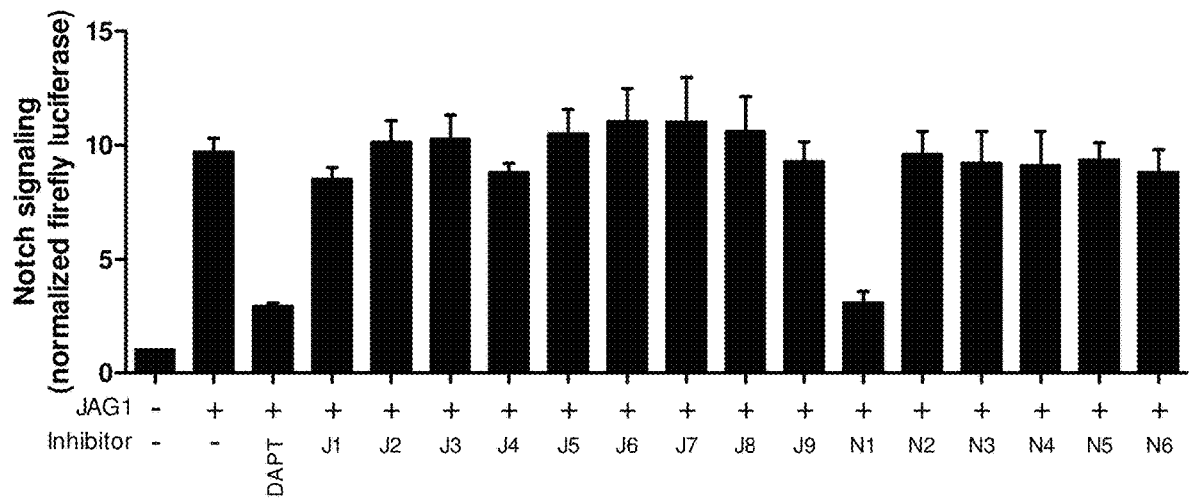
Figure 2C:
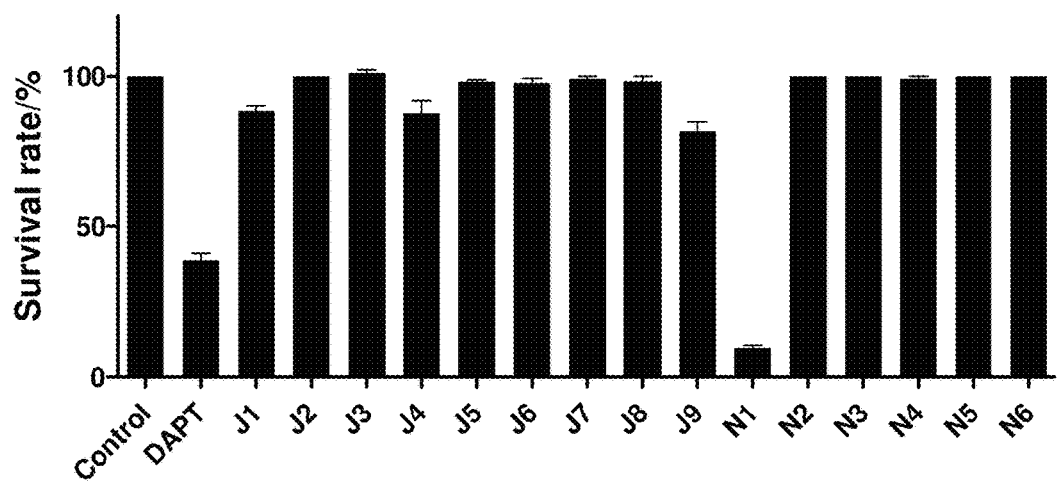
Figure 2D:
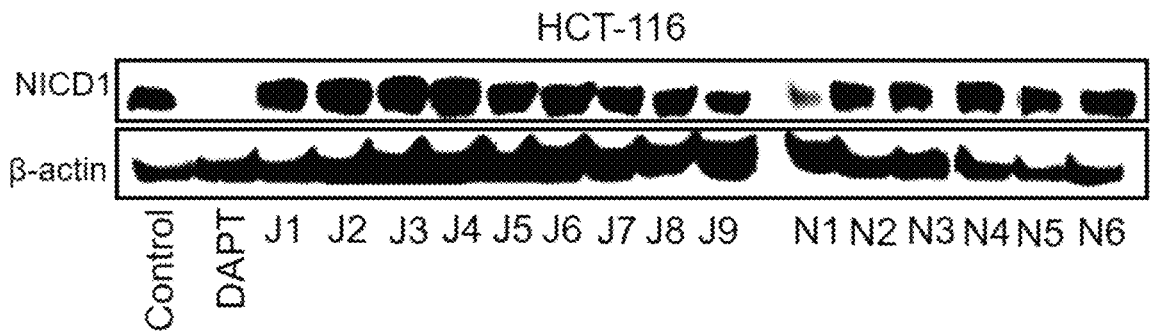
Figure 2E:
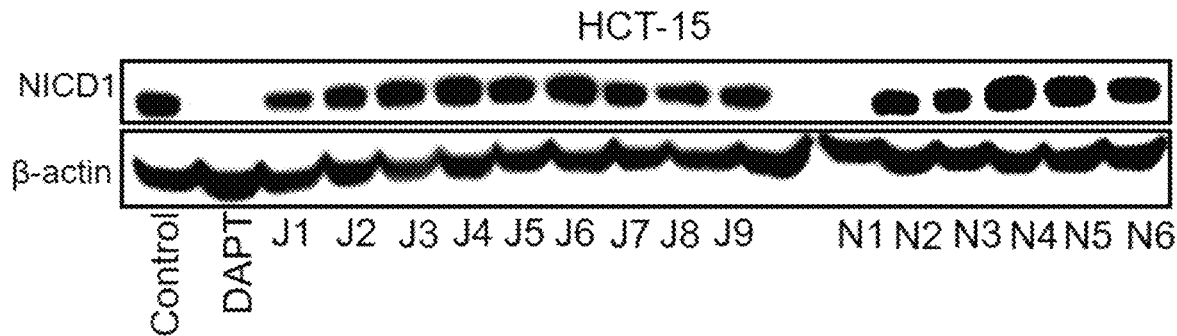

This panel of peptides was also tested for their cytotoxic activities against two human colorectal cell lines (HCT-116 and HCT-15). At a concentration of 100 µM, N1 (SEQ ID NO: 10) is the only peptide that is cytotoxic to HCT-116 and HCT-15 cells (FIGS. 2B and C). Notch signaling results in the release of NICD1 from the membrane-bound Notch receptor. N1 (SEQ ID NO: 10) is also demonstrated as the only peptide which inhibits the formation of NICD1 in HCT-116 (FIG. 2D) or HCT-15 cell lines (FIG. 2E). Both N1 (SEQ ID NO. 10) and positive control DAPT, a gamma-secretase inhibitor, can induce an almost complete elimination of NICD1 (FIGS. 2D and 2E).

N1 (SEQ ID NO. 10) Peptide is Specific in Inhibiting Jag1-Notch1 Signalling

Figure 3A:
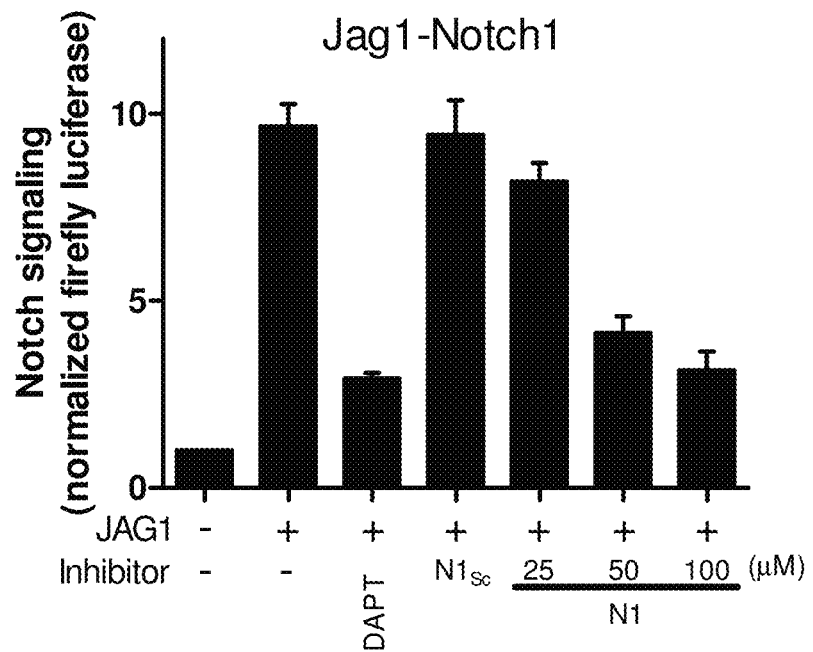
FIG. 3 shows peptide N1 (SEQ ID NO: 10) specifically disrupted Jag1-Notch1 interaction. (A). N1 (SEQ ID NO: 10) peptide inhibited Jag-induced Notch1 signalling in a dose-dependent manner. Half inhibition is reached at between 50 to 100 µM. N1 (SEQ ID NO: 10) peptide cannot inhibit DLL1-Notch1 (B) or DLL4-Notch signalling (C). N1 (SEQ ID NO:10) inhibits Notch1 signalling effectively but does not affect Notch2 signalling. N1 (SEQ ID NO: 10) peptide (50 µM) treatment markedly reduced level of Jag1-induced NICD1 level (D) but has no effect on DLL1-induced NICD1 (E) or DLL4-induced NICD1 level (F). DAPT, as a pan-Notch inhibitor, can inhibit all Jag1-Notch1. DLL1-Notch1 and DLL4-Notch1 signalling. N1 (SEQ ID NO: 10) peptide inhibited signaling through binding to Jag1. Jag1 from HEK293T-Jagged1 cells can be immunoprecipitated by biotinylated N1 (SEQ ID NO: 10) peptide but not to NP (no peptide) or CP (control unrelated peptide) (G).

Specificity of N1 (SEQ ID NO: 10) peptide in inhibiting different Notch ligand-induced Notch signaling was investigated using in vitro co-culture assay. HEK293T or CHO cells expressing Notch ligand (either Jag1, DLL1 or DLL4) are co-cultured with Notch1- or Notch2-expressing cells. Notch1 and Notch2 signalling can be measured by either luciferase reporter assay or by the formation of NICD1 and NICD2. N1 (SEQ ID NO: 10) peptide inhibited Jag1-induced Notch1 signalling in a dose-dependent manner (FIG. 3A). Half inhibition is reached at between 50 to 100 µM. N1 (SEQ ID NO: 10) peptide cannot inhibit DLL1-

TABLE 1

Summary of peptides and their location

| Peptide ID | Peptide sequences | Location Jag 1 | Location Notch 1 | Peptide sequences | Peptide ID |
|---|---|---|---|---|---|
| J1 (SEQ ID No: 1) | CLKEYQSRVTAGCPCSF (S-S) | MNNL | E6F12 | CLDQIGEFQCICMPG | N1 (SEQ ID No: 10) |
| J2 (SEQ ID No: 2) | ESENWPRSY | | | | |
| J3 (SEQ ID No: 3) | FCRPRDDFFGHYAC (S-S) | DSL | EGF11 | CSLGANPCEHAGKC | N2 (SEQ ID No: 11) |
| J4 (SEQ ID No: 4) | CDDYYYGEGCN (S-S) | | | | |
| J5 (SEQ ID No: 5) | CQYGWQGLYC (S-S) | EGF1 | EGF10 | CDTNPVNGKAIC | N3 (SEQ ID No: 12) |
| J6 (SEQ ID No: 6) | CETNWGGQLC (S-S) | EGF2 | EGF9 | CHDRVASFYC | N4 (SEQ ID No: 13) |
| J7 (SEQ ID No: 7) | YCDKCIPHP | EGF2 | EGF9 | CPHGRTGILLC (S-S) | N5 (SEQ ID No: 14) |
| J8 (SEQ ID No: 8) | DLNYC | EGF3 | EGE8 | CVNGWTGEDC (S-S) | N6 (SEQ ID No: 15) |
| J9 (SEQ ID No: 9) | CSNTGPDKYQC | EGF3 | | | |

Screening of Peptides that Disrupt Jag1-Notch1 Interaction

Figure 1B:
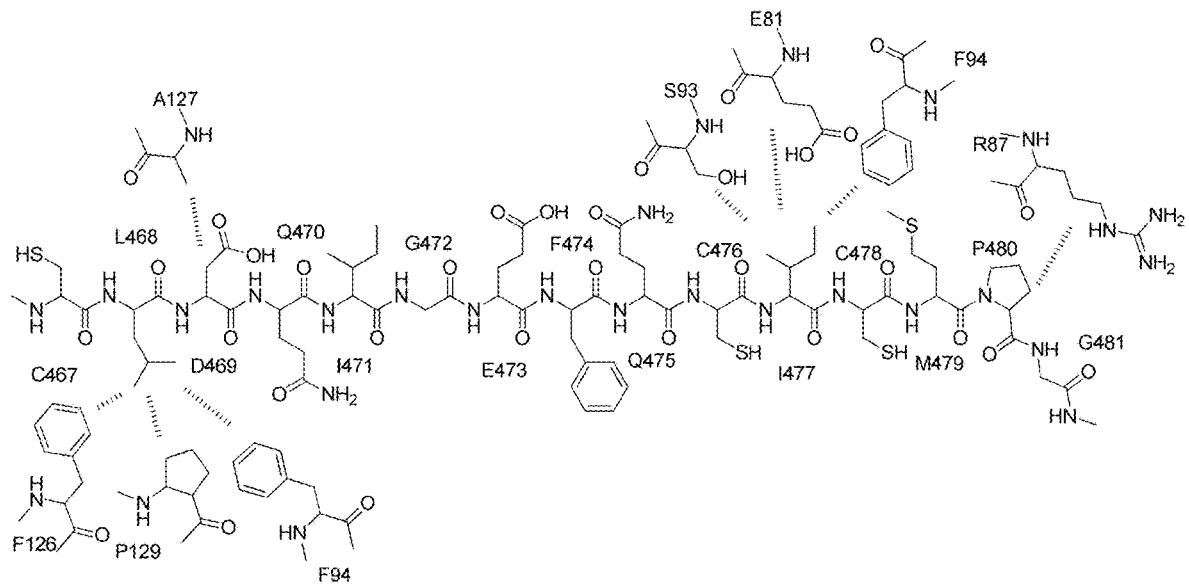
Figure 1C:
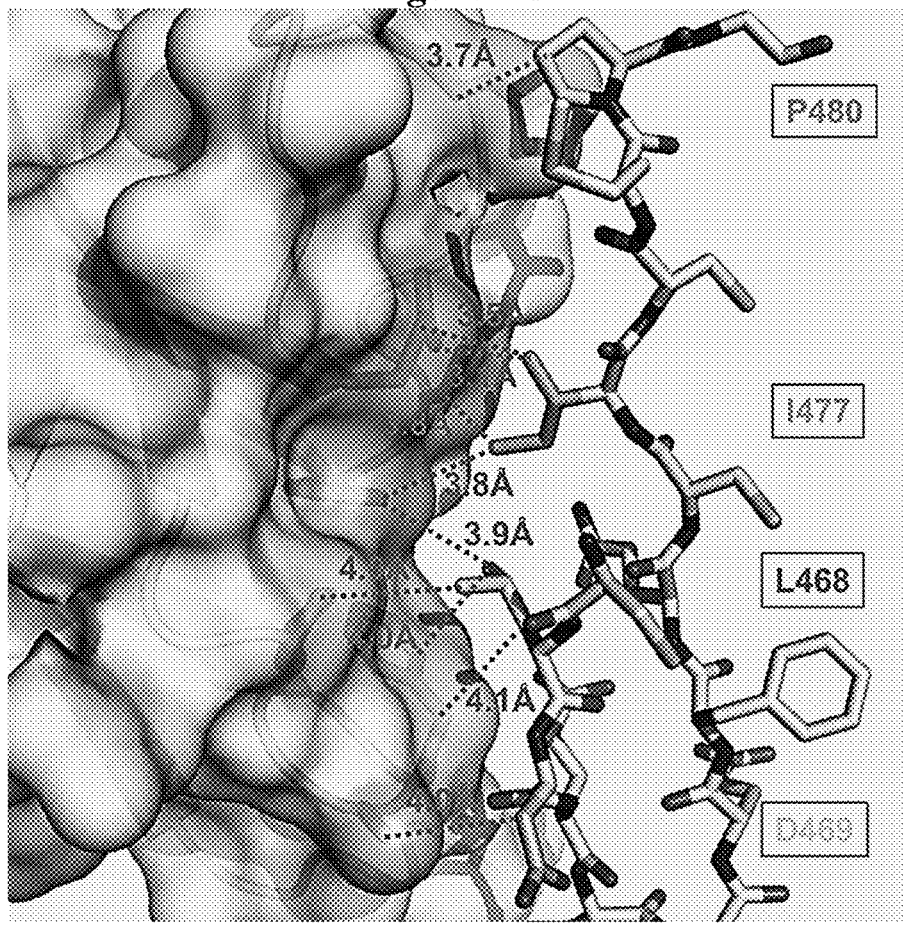
Figure 1D:
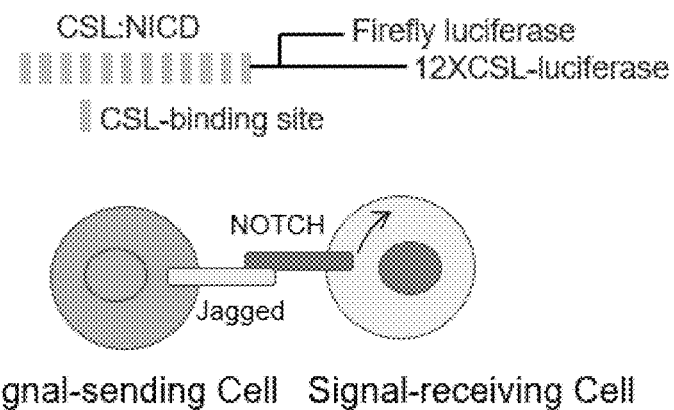

Jag1-Notch interaction is measured using a co-culture assay with one cell line expressing the Notch ligand Jagged1 (Jag1) and a second expressing Notch (either Notch1 or Notch2). A firefly luciferase reporter plasmid with 12 upstream CBF-1 binding site was transfected into signalling-receiving cells to report on Notch signalling (FIG. 1D). Peptides were tested for their activity in inhibiting Jag1-induced Notch signalling. Complete inhibition is equivalent to the background signal seen without induction (−Jag1). Out of the 9 peptides from Jag1 [J1-J9 (SEQ ID NO: 1 to 9)] and 6 from Notch1 [N1-N6 (SEQ ID NO: 10 to 15)], only N1 (SEQ ID NO: 10) can disrupt Jag1-Notch1 signalling (FIG. 2A). N1 (SEQ ID NO: 10) is a 15-mer derived from the EGF-like repeat 12 of Notch1 (C467-G481). This is consistent with the structural information that EGF-like repeat 12 of Notch1 is near the MNNL domain of Jag1 (FIGS. 1B and C).

Figure 3B:
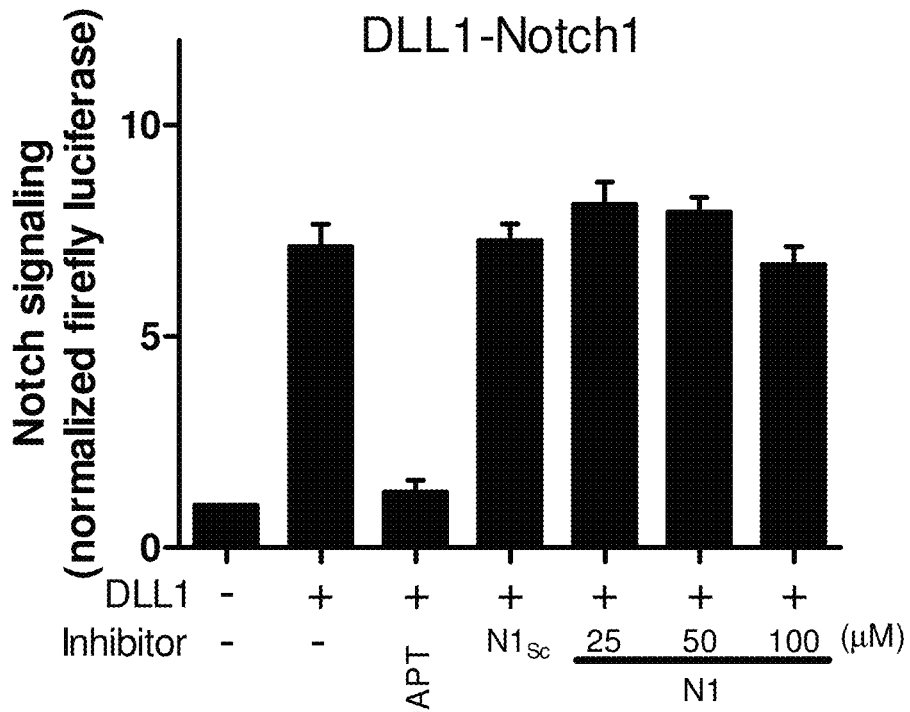
Figure 3C:
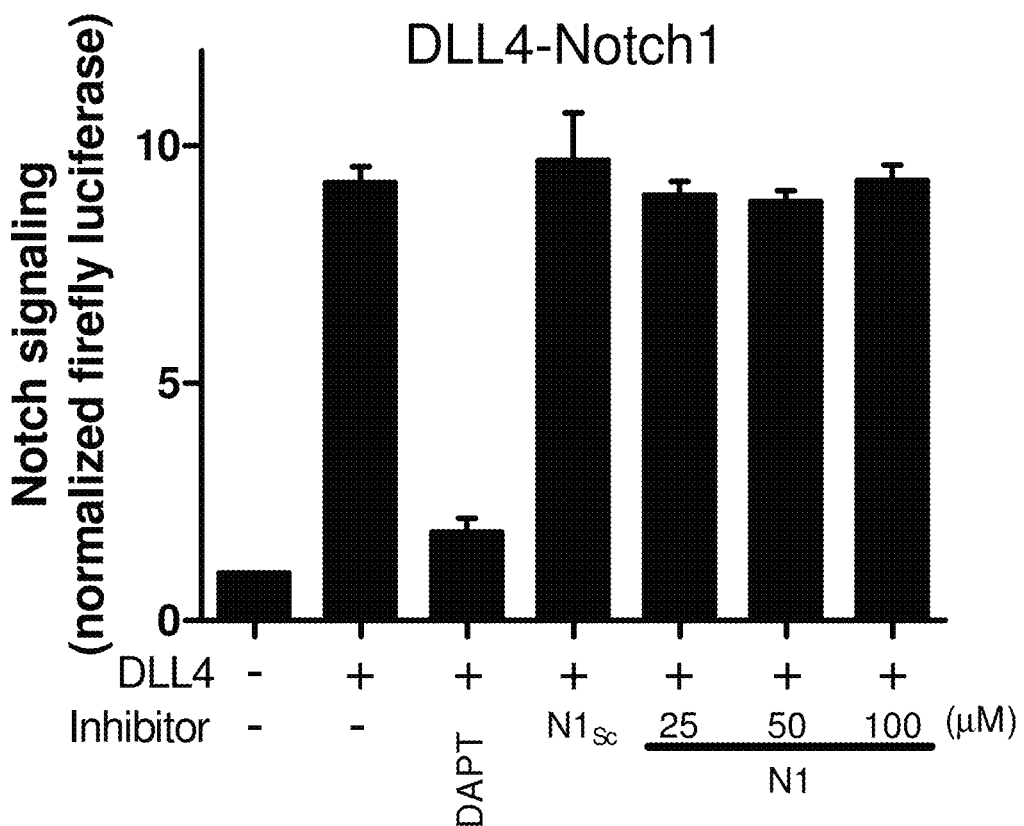
Figure 3D:
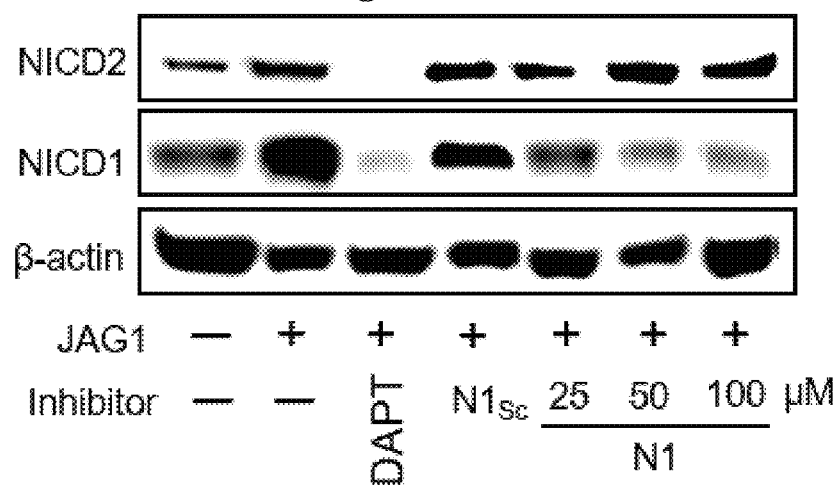
Figure 3E:
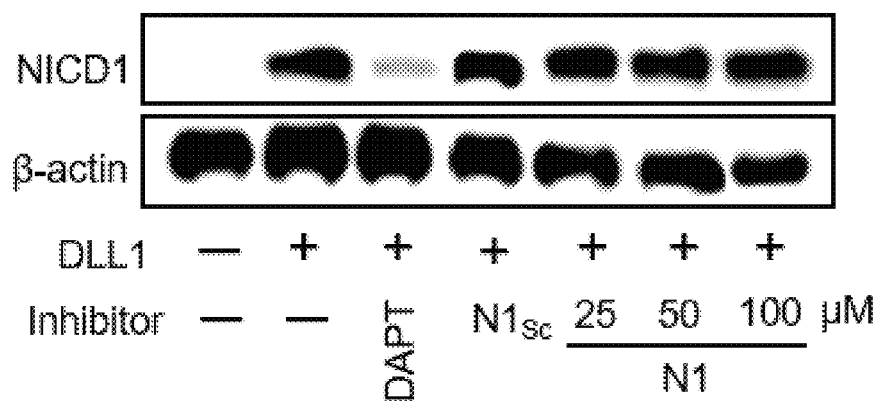
Figure 3F:
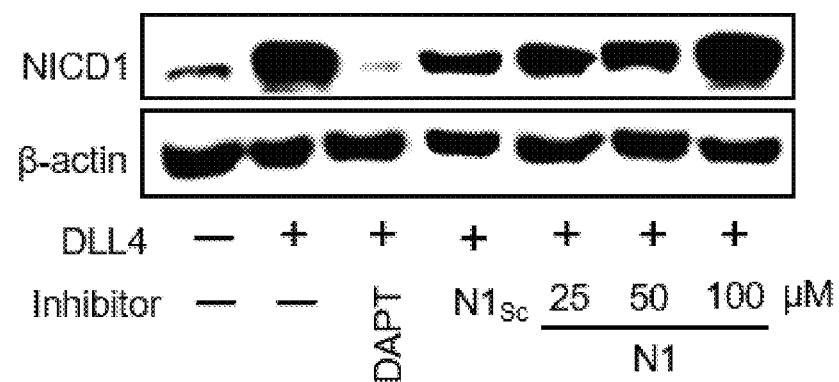
Figure 3G:
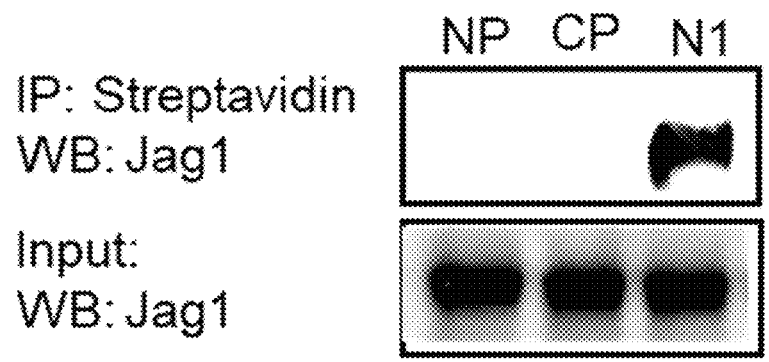

Notch1 (FIG. 3B) or DLL4-Notch1 signaling (FIG. 3C) whereas DAPT can inhibit all signaling (FIGS. 3A, 3B and 3C). While N1 (SEQ ID NO: 10) inhibits Notch1 signalling by inhibiting NICD1 formation, it does not affect NICD2 formation (FIG. 3D). DAPT is equally effective in inhibiting both NICD1 and NICD2 (FIG. 3D). Similarly, N1 (SEQ ID NO: 10) peptide has no effect on DLL-induced NICD1 (FIG. 3E) or DLL4-induced NICD1 level (FIG. 3F) whereas DAPT, as a pan-Notch inhibitor, can inhibit both (FIGS. 3E and 3F). These data demonstrate that N1 (SEQ ID NO: 10) specifically disrupts interaction of Jag1-Notch1 without affecting DLL1-Notch1, DLL4-Notch1 or Jag1-Notch2. This contrasts with DAPT which affects all the above interactions. In addition, the ability of N1 (SEQ ID NO: 10) peptide in binding to Jag1 directly was demonstrated using immunoprecipitation (FIG. 3G).

Optimization of N1 (SEQ ID NO: 10) Peptide

To improve the activity of N1 (SEQ ID NO: 10) peptide, systematic mutation was performed on the interacting residues in N1 (SEQ ID NO: 10). The approach of optimization is to change the interacting residues in N1 (SEQ ID NO: 10) peptide to make a closer or stronger interaction with the Jag1. N1 (SEQ ID NO: 10) peptide sequence and the 4 residues involved in interacting with MNNL domain of Jag1 is shown in FIG. 1B. The following optimization approaches were used to generate N1 (SEQ ID NO: 10) peptide derivatives: (1) The first optimization of N1 (SEQ ID NO: 10) peptide is to determine the minimal length of the peptide needed to disrupt the Jag-Notch1 interaction. The length of N1 (SEQ ID NO: 10) peptide was reduced one residue at a time, from both N and C terminus to determine the minimal length needed for activity. Shorter peptides may offer a better solubility property needed for subsequent animal experiments. Thus, truncated form of N1 (SEQ ID NO: 10) peptides N101 (SEQ ID NO: 17) to N112 (SEQ ID NO: 28) were generated. (2) As P480 is contacting R87 of MNNL of Jag1, it is reasoned that truncation of N1 (SEQ ID NO: 10) at M479 will help the C-terminus to be in a good position to form electrostatic interactions with the side-chain of R87. M479 can also be mutated into an acidic residue (D or E). Therefore, N102 (SEQ ID NO: 18). $N102_{M479E}$ (SEQ ID NO: 34) and $N102_{M479D}$ (SEQ ID NO: 33) were synthesized. (3) As I471 is not contributing to binding with MNNL of Jag1. It is hypothesized that mutation of this into another large hydrophobic residue W would help to improve binding of the peptide to Jag1. Modelling also shows that W471 may form new contacts with P30, L32 and S125 (data not shown). Thus, $N102_{I471W}$ (SEQ ID NO: 35) were synthesized. (4) T466-fucose (originally from EGF repeat of Notch1) makes hydrogen bonds to main-chain carbonyl group of Y82 of MNNL of Jag1. O-linked fucose of T466 of Notch1 is critical in maintaining the contact in the co-crystal structure between the extracellular domains of Jag1 and Notch1 [16]. N1 (SEQ ID NO: 10) was extended to $N1_{T466}$ (SEQ ID NO: 29) and replaced T466 with a residue having a long (as spacer) side-chain which is either positively-charged [$N1_{T466K}$ (SEQ ID NO: 31)], or can form hydrogen bonds [$N1_{T466Q}$ (SEQ ID NO: 32)], or is hydrophobic [$N1_{T466L}$ (SEQ ID NO: 30)].

Figure 4A:
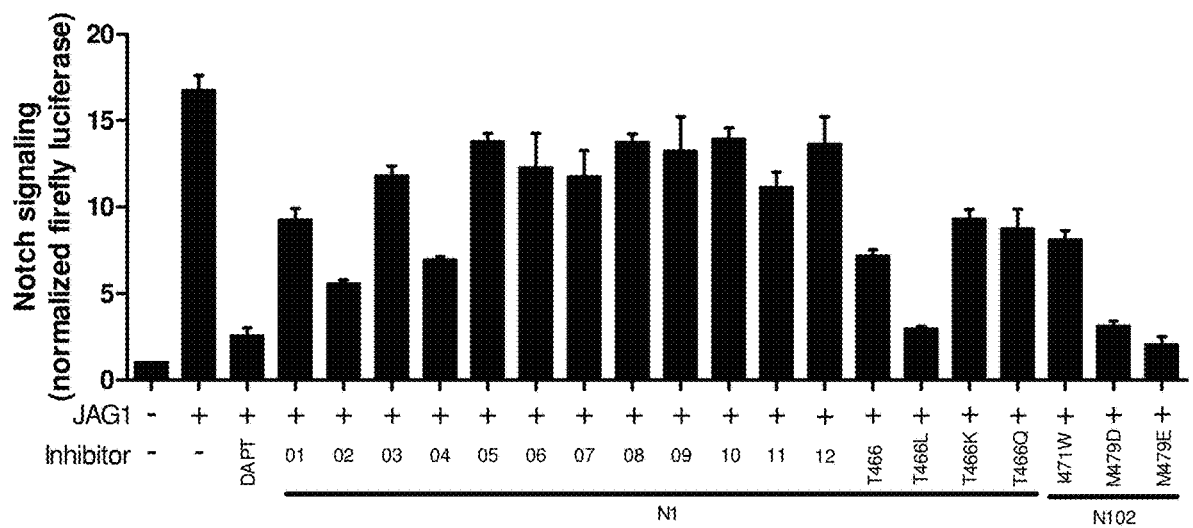
FIG. 4 shows screening of N1 (SEQ ID NO: 10) peptide derivatives for their ability in blocking Jag1-Notch1 signalling. (A) Co-culture assays of Jag1-Notch1 signalling. DAFT 50 µM in DMSO: Peptides, 25 µM in $H_2O$; Values represent Notch reporter gene expression relative to control reporter, normalized to the −JAG1 values. $N102_{M479E}$ (SEQ ID NO: 34) (B), $N102_{M479D}$ (SEQ ID NO: 33) (C) and $N1_{T466L}$ (SEQ ID NO: 30) (D) inhibited Jag1-induced Notch signalling in a dose-dependent manner. DAPT (50 µM in DMSO) was used as positive control. $N102_{M479E}$ (SEQ ID NO: 34) (E). $N102_{M479D}$ (SEQ ID NO: 33) (F) and $N1_{T466L}$ (SEQ ID NO: 30) (G) significantly decreased expression level of NICD1.
Figure 4B:
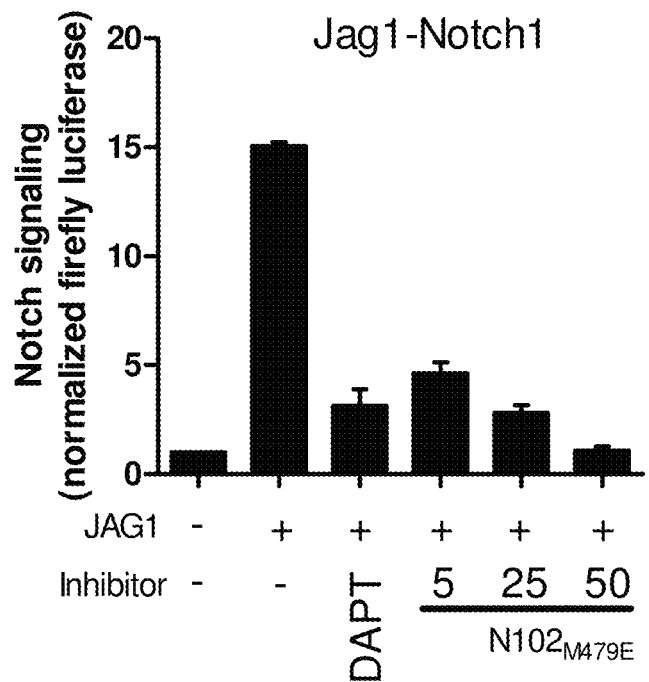
Figure 4C:
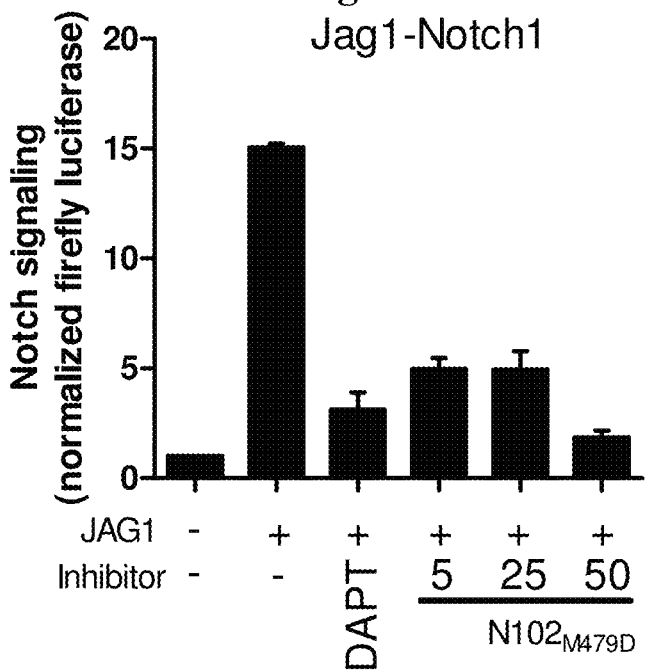
Figure 4D:
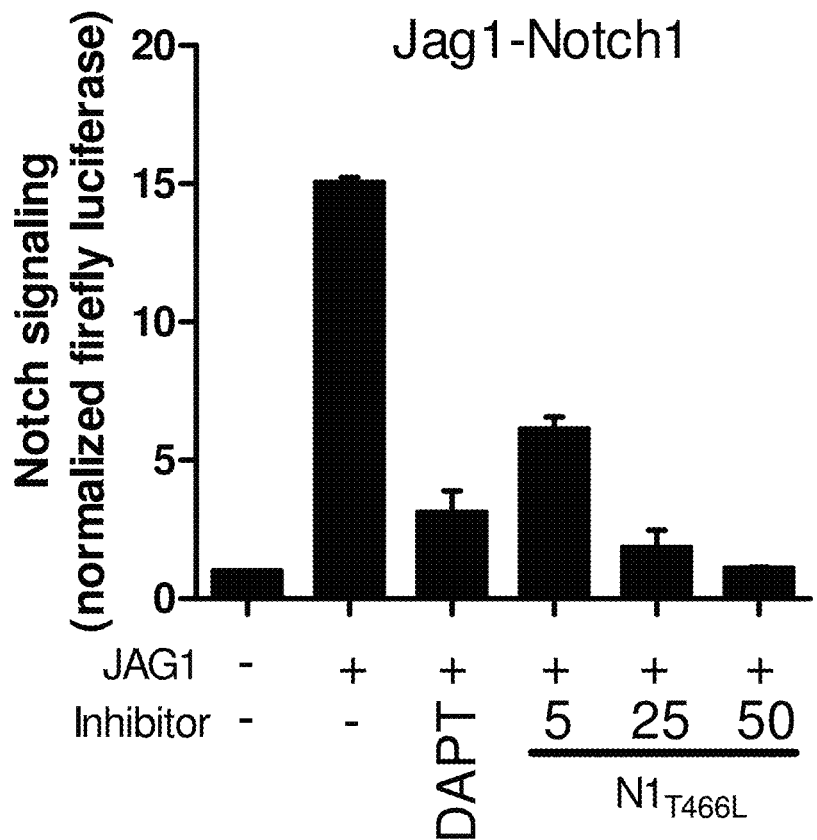
Figure 4E:
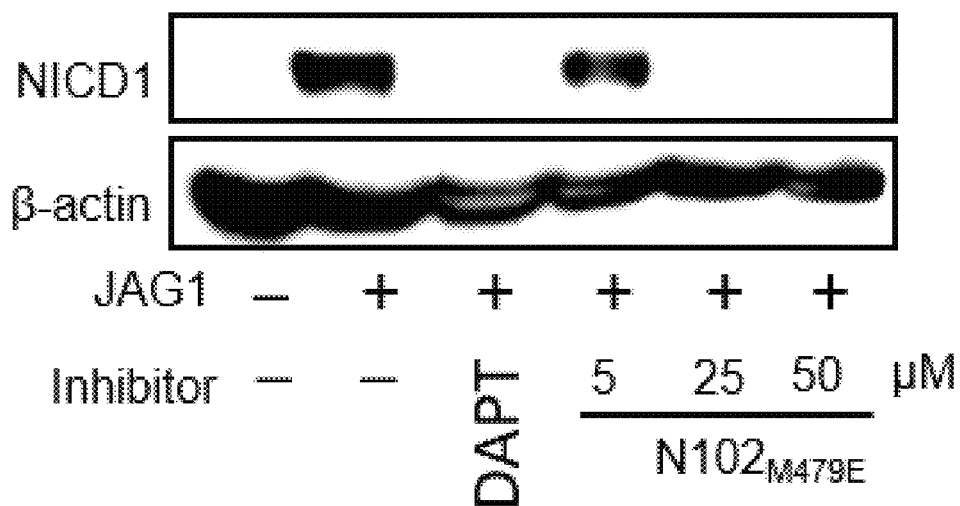
Figure 4F:
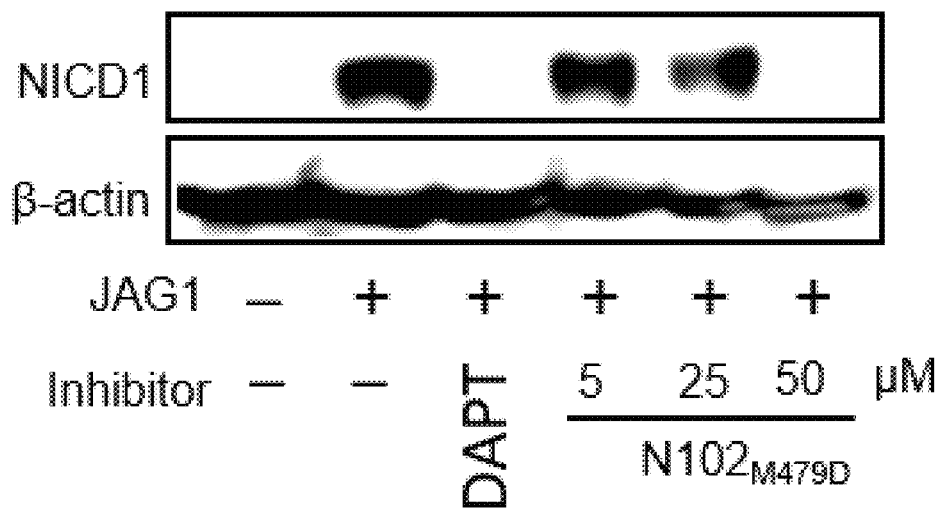
Figure 4G:
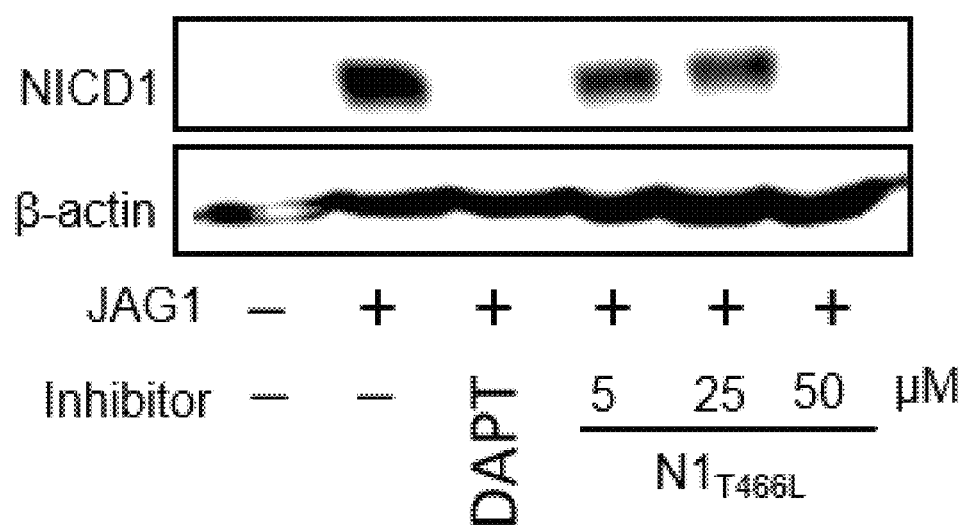
Figure 5A:
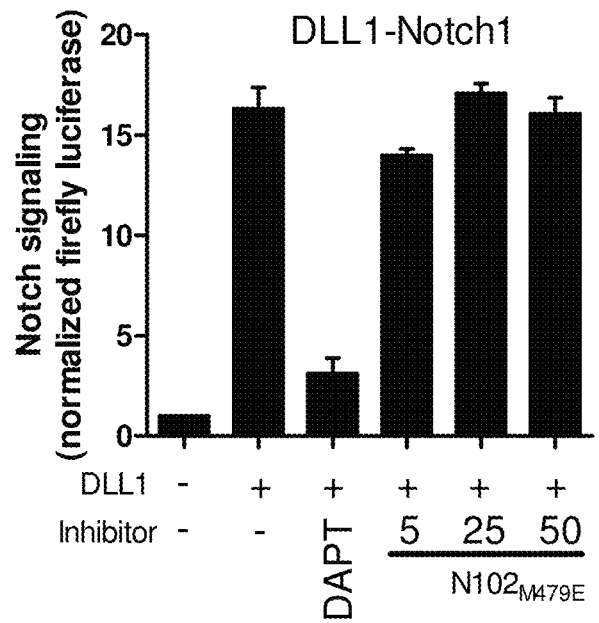
FIG. 5 shows peptide N1 (SEQ ID NO: 10) derivatives are specific in blocking Jag-Notch1 interaction. $N102_{M479E}$ (SEQ ID NO: 34) (A & D), $N102_{M479D}$ (SEQ ID NO: 33) (B & E) and $N1_{T466L}$ (SEQ ID NO: 30) (C & F) have no effects on inhibiting DLL1 (A, B & C) or DLL4-induced (D, E & F) Notch signalling. DAPT (50 µM in DMSO) was used as positive control.
Figure 5B:
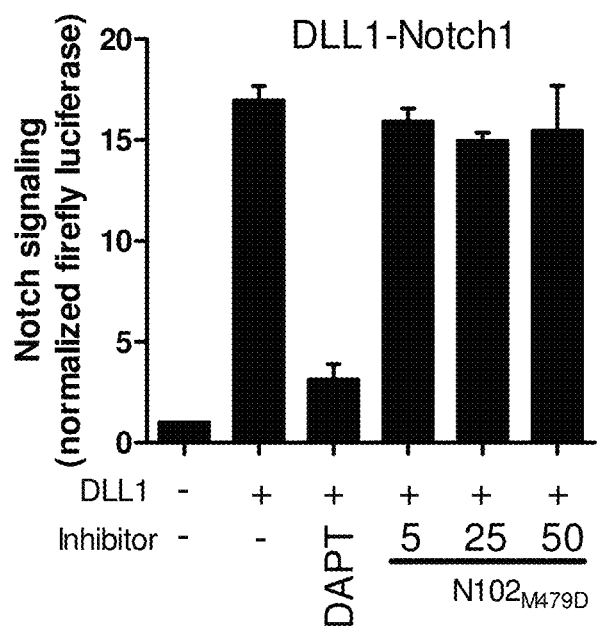
Figure 5C:
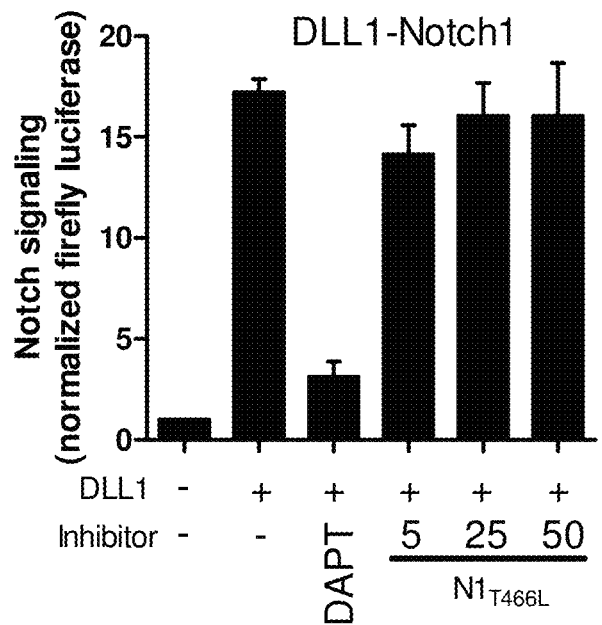
Figure 5D:
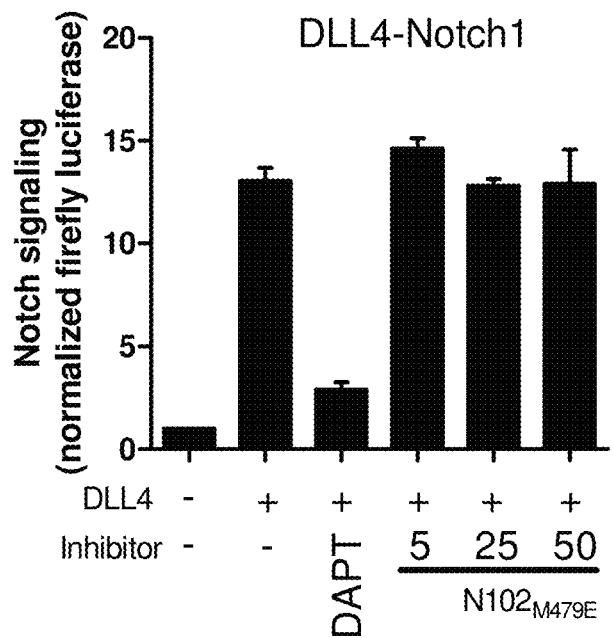
Figure 5E:
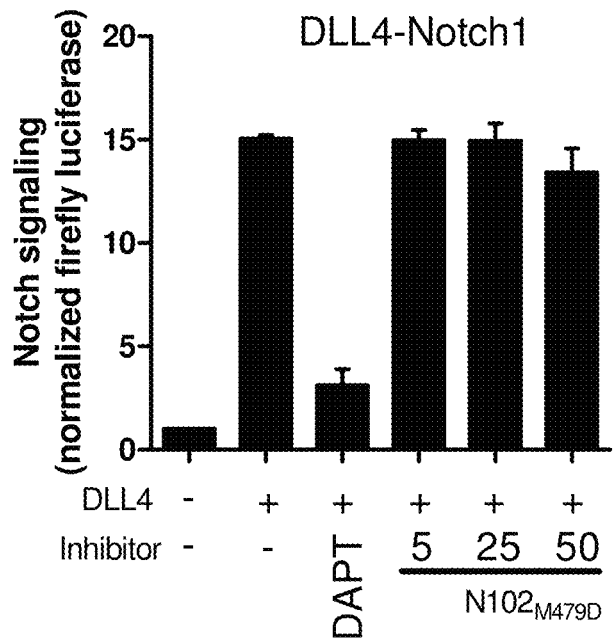
Figure 5F:
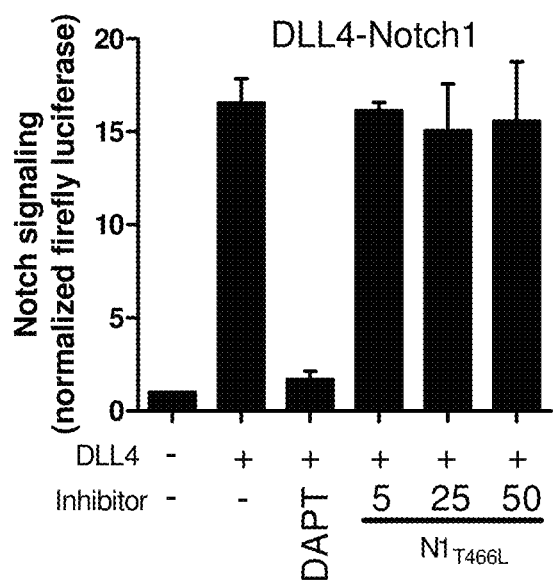

Characterization of N1 (SEO ID NO: 10) Derivatives in Disrupting Jag1-Notch1 Signalling The above N1 (SEQ ID NO: 10) peptide derivatives were tested for activity in inhibiting Jag1 induced Notch signaling using co-culture assays. In general, these peptides displayed varied level of activity in inhibiting Jag1 induced Notch signaling. For truncated N1 (SEQ ID NO: 10) peptide derivatives, N102 (SEQ ID NO: 18) and N104 (SEQ ID NO: 20) exhibited stronger inhibitory effect than N1 (SEQ ID NO: 10). N105 (SEQ ID NO: 21)-N112 (SEQ ID NO: 28) almost lost activity in blocking Jag1-Notch1 signaling. $N1_{T466L}$ (SEQ ID NO: 29). $N1_{T466K}$ (SEQ ID NO: 31). $N1_{T466Q}$ (SEQ ID NO: 32), $N102_{I471W}$ (SEQ ID NO: 35) exhibited slight improvement in inhibiting Notch signaling. The biggest improvement is found in $N1_{T466L}$ (SEQ ID NO: 30). $N102_{M479E}$ (SEQ ID NO: 34) and $N102_{M479D}$ (SEQ ID NO: 33) (FIG. 4A). $N1_{T466L}$ (SEQ ID NO: 30), $N102_{M479E}$ (SEQ ID NO: 34) and $N102_{M479D}$ (SEQ ID NO: 33) inhibited Jag1-induced Notch1 signaling in dose dependent manner as measured by either Notch reporter assay (FIG. 4B. C. D) or NICD1 formation (FIG. 4E, F, G). The specificity of these three active peptides $N1_{T466L}$ (SEQ ID NO: 30). $N102_{M479E}$ (SEQ ID NO: 34) and $N102_{M479D}$ (SEQ ID NO: 33) were also studied in terms of interfering DLL1-Notch1 and DLL4-Notch1 signaling. These peptides did not interfere with DLL1-Notch1 (FIG. 5A, B. C) or DLL4-Notch1 (FIG. 5D, E, F) signaling, suggesting that they were specific to Jag1-Notch.

$N102_{M479E}$ (SEQ ID NO: 34) Effectively Inhibited Proliferation of Human Colon Cancer Cell Lines N1 (SEQ ID NO: 10) peptide inhibited the proliferation of human colon cancer cell line HCT-116 (FIG. 2B) and HCT-15 (FIG. 2C) at 100 µM. N1 (SEQ ID NO: 10) also reduced the colony formation activity in HCT-116 and HCT-15 cells in a dose-dependent manner (data not shown).

Figure 6A:
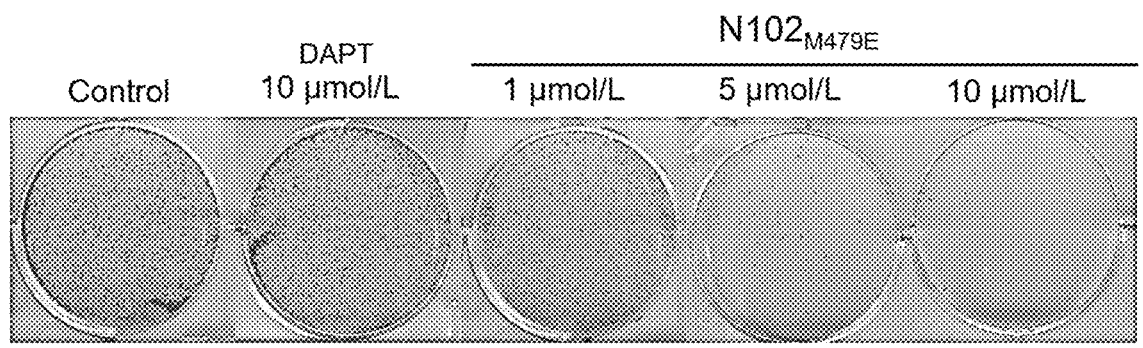
FIG. 6 shows $N102_{M479E}$ (SEQ ID NO: 34) peptide inhibited proliferation of human colon cancer cell line. N1 (SEQ ID NO: 10) reduced the colony formation activity in S1-M1-80 cells in a dose-dependent manner (A). At 10 µM. $N102_{M479E}$ (SEQ ID NO: 34) completely eliminated the formation of colonies. Quantification of colony formation in SI-M1-80 cells treated with DAPT or $N102_{M479E}$ (SEQ ID NO: 34) (B). $N102_{M479E}$ (SEQ ID NO: 34) can effectively downregulate expression of NICD1 in S1-M1-80 cells (C).
Figure 6B:
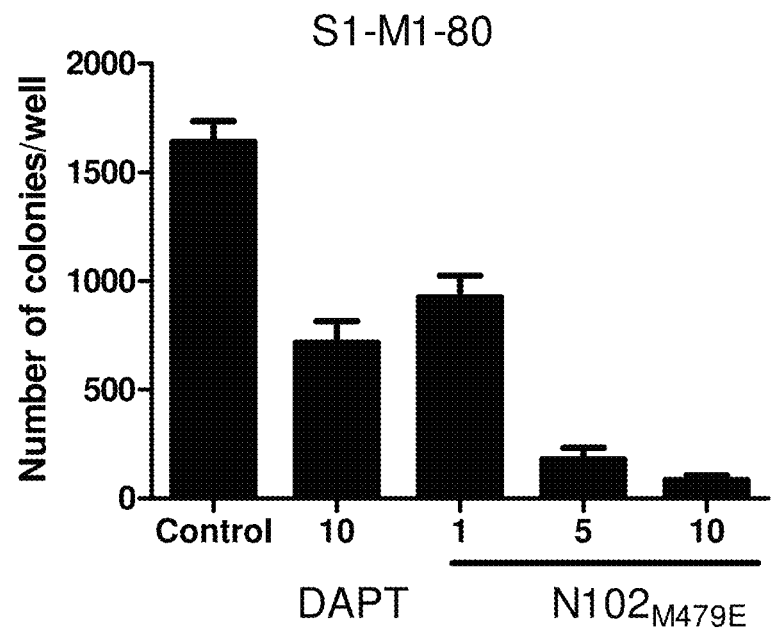
Figure 6C:
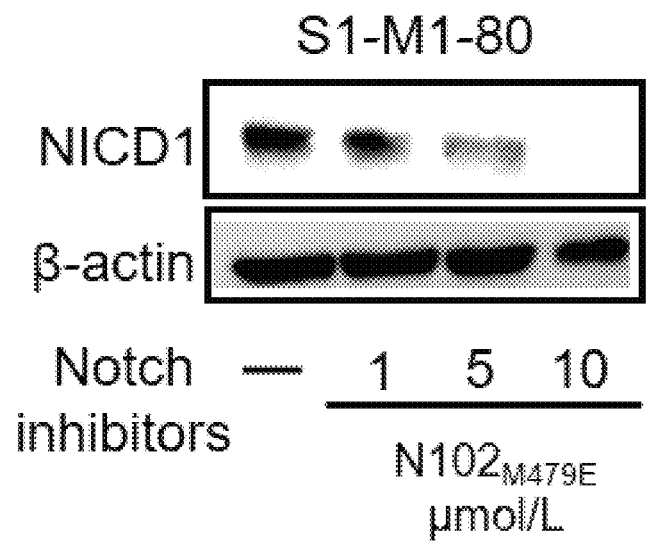
Figure 7:
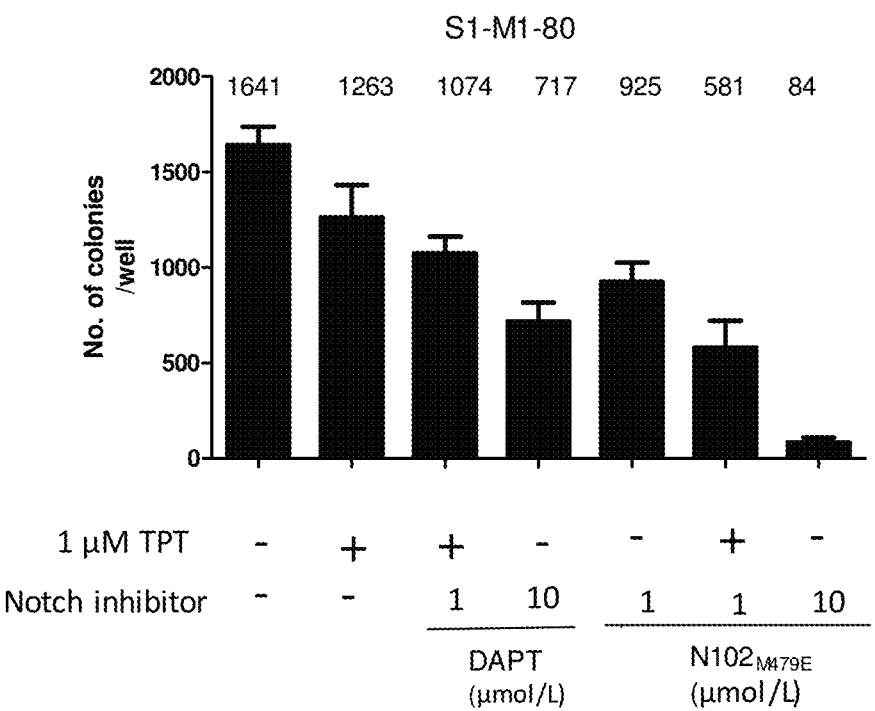
FIG. 7 shows $N102_{M479E}$ peptide (SEQ ID NO: 34) having synergistic effect with topotecan on colony formation activity of S1-M1-80 cells.

Among all N1 (SEQ ID NO: 10) peptide derivatives, the most active $N102_{M479E}$ (SEQ ID NO: 34) was chosen to further study its effect on colony formation of S1-M1-80 cell line. Treatment with $N102_{M479E}$ (SEQ ID NO: 34) effectively reduced colony formation of S-M1-80 in a dose-dependent manner. At 1 µM, colony formation can be reduced by half. At 5 µM, $N102_{M479E}$ (SEQ ID NO: 34) almost eliminated the formation of all colonies (FIGS. 6A and B). $N102_{M479E}$ (SEQ ID NO: 34) can totally suppress NICD1 formation in S1-M1-80 cells at 10 µM (FIG. 6C).

Cytotoxicity Profile of Peptides

To determine the anti-proliferative effect of peptides towards human colon cancer cell lines. Cytotoxicity of all peptides was tested toward colon cancer cell lines HCT-116 and S1-M1-80 (Table.2). Cytotoxicity of peptides to colon cancer cells is associated with activity of disrupting Jag1-Notch1 interaction. Those peptides active in blocking Jag1-Notch1 interaction can also inhibit cell proliferation of HCT-116 and S1-M1-80 cells. N1 (SEQ ID NO: 10) peptide and derivatives including $N1_{T466L}$ (SEQ ID NO: 30), $N102_{M479E}$ (SEQ ID NO: 34), $N102_{M479D}$ (SEQ ID NO: 33). $N102_{T466L-M479E}$ (SEQ ID NO: 36), $N102_{T466I-M479E}$ (SEQ ID NO: 37), $N102_{T466W-479E}$ (SEQ ID NO: 38), $N102_{T466F-M479E}$ (SEQ ID NO: 39). $N102_{T466Y-M479E}$ (SEQ ID NO: 40) effectively inhibited proliferation of HCT-116 and S1-M1-80. They exhibited varied $IC_{50}$ values ranging from 3.9±0.3 µM to 47.3 t 3.1 µM, with nearly comparable potency as topotecan (Table 2). In terms of intrinsic cytotoxicity to normal cells, most of the active peptides [$N1_{T46L}$ (SEQ ID NO: 30), $N102_{M479E}$ (SEQ ID NO: 34), $N102_{M479D}$ (SEQ ID NO: 33). $N102_{T466L-M479E}$ (SEQ ID NO: 36). $N102_{T466I-M479E}$ (SEQ ID NO: 37). $N102_{T466W-M479E}$ (SEQ ID NO: 38). $N102_{T466F-M479E}$ (SEQ ID NO: 39). $N102_{T466Y-M479E}$ (SEQ ID NO: 40)] are non-toxic to mouse fibroblast L929 cells or HEK-293T-Jagged-1 cells as their $IC_{50}$ values were above 100 µM, indicating that these active peptides are potential anti-cancer candidates in view of their low toxicity to normal cells. The above data demonstrated that $N102_{M479E}$ (SEQ ID NO: 34) is a promising candidate for treating colorectal cancer and merit further studies in in vivo efficacy experiments.

Synergistic Effect with Anti-Cancer Drug

The peptides of this invention is demonstrated to have synergistic effect with existing anti-cancer drug. Topotecan (TPT) and $N102_{M479E}$ (SEQ ID NO: 34) were chosen as examples to illustrate this aspect of the invention. S-M1-80 is a TPT-resistant cell line (colony formation=1641 colonies/well) and colony formation activity of S1-M1-80 cells was used as a measure for the synergistic effect.

Treatment with 1 µM of TPT reduced colony formation slightly (1263 colonies/well). Combination of 1 µM of TPT with 1 µM DAPT can further reduce it to 1074 colonies/well. Treatment of 10 µM of DAPT can reduce it to 717 colonies/well.

Treatment with 1 µM of $N102_{M479E}$ (SEQ ID NO: 34) can reduce colony formation to 925 colonies/well, indicating that $N102_{M479E}$ (SEQ ID NO: 34) is 14% more potent than DAPT. Combination of 1 µM of TPT with $N102_{M479E}$ can further reduce it to 581 colonies/well, an increase in 19% of potency over TPT-DAPT combination. Treatment of 10 μM of N102$_{M479E}$ (SEQ ID NO: 34) was very potent (84 colonies/well), representing an increase in potency of about 88% over DAPT.

The above results suggest that TPT and N102$_{M479E}$ (SEQ ID NO: 34) are synergistic in reducing colony formation of S1-M1-80, with an improvement of 19% in potency over TPT-DAPT combination. Use of N102$_{M479E}$ (SEQ ID NO: 34) alone is 88% more potent than DAPT.

TABLE 2

Summary of sequences and cytotoxicity of peptides.

| SEQ ID No. | Topotecan DAPT | Sequence | S1 | IC$_{50}$ (μM) s1-m1-80 | HEK-293T-Jagged-1 |
|---|---|---|---|---|---|
| | | — | 0.19 ± 0.05 | 14.9 ± 0.1 | ND |
| | | — | >100 | 17.1 ± 0.4 | ND |
| 1 | J1 | CLKEYQSPVTAGGPCSF (S-S) | ND | ND | ND |
| 2 | J2 | FSFAWPRSY | ND | ND | ND |
| 3 | J3 | FCRPRDDFFGHYAC (S-S) | ND | ND | ND |
| 4 | J4 | CDDYYYGFGCN (S-S) | ND | ND | ND |
| 5 | J5 | CQYGWQGLYC (S-S) | ND | ND | ND |
| 6 | J6 | CETNWGGQLC (S-S) | ND | ND | ND |
| 7 | J7 | YCDKCIPHP | ND | ND | ND |
| 8 | J8 | DLNYC | ND | ND | ND |
| 9 | J9 | CSNTGPDKYQC | ND | ND | ND |
| 10 | N1 | CLDQIGEFQCICMPG | >50 | 16.3 ± 0.6 | ND |
| 11 | N2 | CSLGANPCEHAGKC | ND | ND | ND |
| 12 | N3 | CDTNPVNGKAIC | ND | ND | ND |
| 13 | N4 | CHDRVASFYC | ND | ND | ND |
| 14 | N5 | CPHGRTGLLC (S-S) | ND | ND | ND |
| 15 | N6 | CVNGWTGEDC (S-S) | ND | ND | ND |
| 16 | N1sc | QPGIICDMQFLGCCE | ND | ND | ND |
| 17 | N101 | CLDQIGEFQCICMP | >50 | 14.1 ± 0.7 | ND |
| 18 | N102 | CLDQIGEFQCICM | >50 | 10.2 ± 0.4 | ND |
| 19 | N103 | CLDQIGEFQCIC | >100 | >50 | ND |
| 20 | N104 | CLDQIGEFQCI | >50 | 28.4 ± 0.6 | ND |
| 21 | N105 | CLDQIGEFQC | >100 | >100 | ND |
| 22 | N106 | CLDQIGEFQ | >100 | >100 | ND |
| 23 | N107 | CLDQIGEF | >100 | >100 | ND |
| 24 | N108 | CLDQIGE | >100 | >100 | ND |
| 25 | N109 | CLDQIG | >100 | >100 | ND |
| 25 | N110 | CLDQI | >100 | >100 | ND |
| 27 | N111 | CLDQ | >100 | >100 | ND |
| 28 | N112 | IGEFQCICMPG | >100 | >100 | ND |
| 29 | N1$_{T466}$ | TCLDQIGEFQCICMPG | >100 | >50 | ND |
| 30 | N1$_{T466L}$ | LCLDQIGEFQCICMPG | >50 | 8.2 ± 0.3 | >100 |
| 31 | N1$_{T466K}$ | KCLDQIGEFQCICMPG | >100 | >50 | ND |
| 32 | N1$_{T466Q}$ | QCLDQIGEFQCICMPG | >100 | >50 | ND |

TABLE 2-continued

Summary of sequences and cytotoxicity of peptides.

| SEQ ID No. | Topotecan DAPT | Sequence | S1 | IC$_{50}$ (μM) s1-m1-80 | HEK-293T-Jagged-1 |
|---|---|---|---|---|---|
| 33 | N102$_{m479D}$ | CLDQIGEFQCICD | >50 | 5.8 ± 0.2 | >100 |
| 34 | N102$_{m479E}$ | CLDQIGEFQCICE | >30 | 4.9 ± 0.2 | >100 |
| 35 | N102$_{I471w}$ | CLDQWGEFQCICM | >100 | >50 | ND |
| 36 | N102$_{T466L-M479E}$ | LCLDQIGEFQCICE | ND | 5.4 ± 1.2 | >100 |
| 37 | N102$_{T466I-M479E}$ | ICLDQIGEFQCICE | ND | 15.2 ± 4.2 | >100 |
| 38 | N102$_{T466W-M479E}$ | WCLDQIGEFQCICE | ND | 54.3 ± 5.2 | >100 |
| 39 | N102$_{T466F-M479E}$ | FCLDQIGEFQCICE | ND | 43.9 ± 3.4 | >100 |
| 40 | N102$_{T488Y-M479E}$ | YCLDQIGEFQCICE | ND | 14.9 ± 4.8 | >100 |

The IC$_{50}$ value was determined after exposure to topotecan, DAPT, and peptides using HCT-116, S1-M1-80, HEK293T-Jagged1 and L929 cells, as described in the Materials and Methods section. N=1-3 independent experiment and the values were presented as mean±standard error of mean. ND=not determined.

This invention provides a synthetic peptide for specific inhibition of Jag1-Notch1 signaling. In one embodiment, said synthetic peptide having a sequence Z$_1$-CLDQI-GEFQCI-Z, wherein: Z$_1$ is selected from hydrogen, F, I, L, W and Y; Z is —OH or a sequence of up to 5 amino acids selected from D, E, G, M and P (SEQ ID NO: 41), or a sequence of up to 5 amino acids beginning with C followed by at least one amino acid selected from M, P, D, E and G (SEQ ID NO: 42).

In one embodiment, said sequence is selected from the group consisting of N1 (SEQ ID NO: 10), N101 (SEQ ID NO: 17), N102 (SEQ ID NO: 18), N104 (SEQ ID NO: 20), N1$_{T466L}$ (SEQ ID NO: 30), N102$_{M479D}$ (SEQ ID NO: 33), N102$_{M479E}$ (SEQ ID NO: 34) N102$_{T466L-M479E}$ (SEQ ID NO: 36), N102$_{T466I-M479E}$ (SEQ ID NO: 37), N102$_{T466W-M479E}$ (SEQ ID NO: 38), N102$_{T466F-M479E}$ (SEQ ID NO: 39), and N102$_{T466Y-M479E}$ (SEQ ID NO: 40).

In one embodiment, said synthetic peptide has a fucose binding at T466.

In one embodiment, said sequence is Z$_1$-CLDQI-GEFQCIC-Z$_2$, wherein Z$_2$ is a negatively charged amino acid (SEQ ID NO: 43).

In one embodiment, the synthetic peptide above has an affinity to the MNNL domain of Jag1.

This invention further provides a composition comprising the any of the synthetic peptide mentioned above. In one embodiment, said composition further comprises fucose and/or an anti-cancer drug. In one embodiment, said anti-cancer drug is selected from the group consisting of topotecan, 5-fluorouracil, capecitabine, irinotecan, oxaliplatin, doxorubicin, paclitaxel, carmustine, Bevacizumab, lomustine and temozolomide.

This invention also provides the use of the synthetic peptide mentioned herein for the preparation of a medicament for treating a subject with a disease responsive to Jag1-Notch1 signaling inhibition, wherein said disease is selected from the group consisting of lymphoma, colorectal cancer and glioblastoma.

The invention further provides the use of any of the synthetic peptides mentioned herein for treating a subject with a disease responsive to Jag1-Notch1 signaling inhibition, wherein said disease is selected from the group consisting of lymphoma, colorectal cancer and glioblastoma. In one embodiment, the use of the synthetic peptides further comprises co-administering fucose and/or an anti-cancer drug. In another embodiment, said anti-cancer drug is selected from the group consisting of topotecan, 5-fluorouracil, capecitabine, irinotecan, oxaliplatin, doxorubicin, paclitaxel, carmustine, Bevacizumab, lomustine and temozolomide.

This invention also provides a method for disrupting Jag1-Notch1 signaling between a signal-sending cell and a signal-receiving cell, comprising contacting said signal-sending cell with any of the synthetic peptides mentioned herein. In one embodiment, said method further comprises co-administering fucose. In another embodiment, said synthetic peptide contacts Jag1 of said signal-sending cell. In a further embodiment, said cell is a tumor cell. In yet another embodiment, said tumor cell is from a tumor selected from the group consisting of lymphoma, glioblastoma and colorectal cancer.

This invention further provides a method of treating a subject with a disease responsive to Jag1-Notch1 signaling inhibition, comprising administering an effective amount of any of the synthetic peptides mentioned herein to said subject, wherein said disease is selected from the group consisting of lymphoma, colorectal cancer and glioblastoma.

Examples

Material and Methods

Chemicals and Inhibitors

All chemical used in this study were pure compound in powder form and commercially available. N—[N-(3,5-Difluorophenacetyl)-L-alanyl]-S-phenylglycine t-butyl ester (DAPT) in white powder was purchased from TCI (Shanghai), Shanghai, China. Topotecan (powder, purity >98%) was purchased from TC (Shanghai), Shanghai, China. Dulbecco's Modified Eagle Medium (DMEM), Roswell Park Memorial Institute (RPMI) 1640 medium, trypsin/EDTA acid and penicillin/streptomycin (P/S) were purchased from Gibco. Fetal bovine serum (FBS) was obtained from HyClone. All other common reagents were purchased from Sigma-Aldrich.

Peptide Library

The oligo-peptides are derived from Jag1-Notch1 binary complex from the extracellular domain. Each peptide represented a unique binding site on the extracellular domain. Their sequences were 5 to 17 amino acids in length and spanned from Jag-1 MNNL to EGF-like 3 as well as Notch-1 EGF-like 8-12. The peptide library consists of linear and di-sulfide cyclized peptides. All the synthetic peptides used are synthesized by traditional Fmoc solid-phase synthesis. The peptides used in this study were synthesized by Ming-Hao, Wuhan, China. The peptides were dissolved in deionized $H_2O$ or 1×PBS to bring the concentration to 5 mM. The biotinylated peptides for pull-down assays were also purchased from the same vendor.

Cell Lines and Cell Culture

The passages of all cell lines used in this study were within 5 to 10 from thawing them on. In this study, Human colon cancer cell line HCT-116 (ATCC® CCL-247™) and HCT-15 (ATCC® CCL-225™). HEK293T-Jagged-1. CHO-DLL4, CHO-DLL, S1-M1-80. Mouse L929 fibroblastic cell lines were used in the experiments. The human embryonic kidney cells 293T stably expressed full length human Jagged-1 (HEK293T-Jagged-1) was kindly provide by Prof. Urban Lendahl (Karolinska Institute, Sweden). The Chinese hamster ovary (CHO) cells stably expressed human full length DLL1 (CHO-DLL1) and the Chinese hamster ovary (CHO) cells stably expressed human full length DLL4 (CHO-DLL4) were kindly provided by Prof. Achim Gossler (Hannover medical school. German). The human colon carcinoma cell line S1-M1-80 was a mitoxantrone derivative of S1 and was kindly provided by Prof. Kenneth To (The Chinese University of Hong Kong, Hong Kong).

L929 and HEK293T-Jagged-1 cell line were cultured in supplemented DMEM media with 10% heat inactivated FBS, penicillin (100 U/mL). HCT-116. HCT-15 were cultured in supplemented RPMI media with 10% heat inactivated FBS, penicillin (100 U/mL). S1-M1-80 cell lines were cultured in supplemented MEM media with 10% heat inactivated FBS, penicillin (100 U/mL). All cells were maintained at 37 with 5% CO2 in a humidified incubator.

Plasmids

Luciferase reporter plasmid with 12× wild-type CBF1 binding sites and pTK-*Renilla* Luciferase plasmid was used in this study. 12×CSL-Firefly luciferase plasmid was a kind gift from Prof. Urban Lendahl (Karolinska Institute, Sweden). *Renilla* luciferase plasmid was purchased from Promega Corporation.

Cellular Co-Culture Assay

HEK-293T-Jagged-1 cells were seeded in 24-well plates in triplicate per sample group, and human HCT-116 cells were seeded in one 60 mm dish. Cells were allowed to settle, and were transfected the following day after the medium was changed to be antibiotic free. HCT-116 cells were transfected with 12×CSL-Luc and *Renilla*-Luc, using Lipofectamine® 3000 (Invitrogen™), according to the manufacturer's instructions. After 24 hours, HCT-116 cells were scraped and $2.5 \times 10^4$ cells in 1 mL complete medium per well were added to both 24-well plates. Peptides were treated to cells with the desired concentrations. N—[N-(3, 5-difluorophenacetyl)-L-alanyl]-S-phenylglycine t-butyl ester (DAPT) was used as positive control. Cells were co-cultured for 12 hours before measure the luciferase activity. After incubation, cells were lysed with luciferase lysis buffer. Notch activity in cells expressing the 12×CSL-Luc reporter construct was measured by a luciferase assay using Dual-Luciferase® Reporter Assay System (Promega).

Cell Proliferation Assay

HCT-116, HCT-15, S1-M1-80, S1, L929, HEK293T-Jagged-1 were seeded in each well of a 96-well plate with a series of concentrations (a serial dilution from 1000μM to 0.5 μM) of peptides or drugs including DAPT, Topotecan at 37° C. with 5% CO2 in a humidified incubator for 3 days. Percentage of survival was determined by MTS assay as described.

In Vitro Pull-Down Assay

HEK293T-Jagged1 cells were lysed in 1×RIPA lysis buffer (20 mMTris-HCl (pH 7.5) 150 mM NaCl, 1 mM $Na_2EDTA$, 1 mM EGTA, 1% NP-40, 1% sodium deoxycholate, 2.5 mM sodium pyrophosphate, 1 mM β-glycerophosphate, 1 mM $Na_3VO_4$). One microgram of biotin-labeled peptides and streptavidin-conjugated magnetic beads (Promega) was used to pull down human Jag1. The resulting proteins were resolved on SDS-PAGE and detected with an anti-Jagged1 antibody.

Antibodies

The cleaved Notch1 (Val1744) (D3B8) rabbit monoclonal antibody (CST) and Notch2 (Cleaved Ala1734) rabbit monoclonal antibody at 1:1000 dilution were used to detect human Notch intracellular domain (NICD1) and Notch2 intracellular domain (NICD2), respectively. β-actin was detected using a mouse monoclonal antibody (Santa Cruz Biotechnology) at 1:3000 dilution.

Clonogenicity Assay

The procedure for colony formation assay consists of following steps. An appropriate number of cells per well were seeded on a 6-well plate in duplicate. The number of cells for seeding should be related to the aggressiveness of the treatment. The cells were incubated for 12 hours in a CO2 incubator at 37° C. and allow cells to attach to the plate. The cells were treated with peptides or (DAPT) to required concentrations. The cells were incubated in a in a CO2 incubator at 37° C. for about 10 days until cells in control well have formed colonies which are of a substantially good size (the minimum score is 100 cells per colony). After the incubation, the medium was removed and cells were rinsed with 5 ml 1×PBS (phosphate buffered saline. pH 7.2). The cells were then fixed with 1 ml methanol at room temperature for 10 min. After fixation, the cells were stained with 0.5% crystal violet solution and incubated at room temperature for 1 h. After staining, the plates were immersed in deionized water to rinse off crystal violet and air-dried at room temperature for overnight. The dry plates were pictured with scanner. The number of colonies in each well was counted by cell counter software.

REFERENCES

1. Ellisen, L. W., et al., TAN-1 the human homolog of the *Drosophila* Notch gene, is broken by chromosomal translocations in T lymphoblastic neoplasms. Cell, 1991. 66(4): p. 649-661.
2. Reedijk. M., et al., Activation of Notch signaling in human colon adenocarcinoma. Int J Oncol, 2008. 33(6): p. 1223-9.
3. Veenendaal, L. M., et al., Differential Notch and TGFbeta signaling in primary colorectal tumors and their corresponding metastases. Cell Oncol, 2008. 30(1): p. 1-11.
4. Dai, Y., et al., Silencing of Jagged1 inhibits cell growth and invasion in colorectal cancer. Cell Death Dis, 2014. 5: p. e1170.
5. Gao. J., et al., Up-regulated expression of Notch1 and Jagged1 in human colon adenocarcinoma. Pathol Biol (Paris), 2011. 59(6): p. 298-302.

6. Rodilla, V., et al., Jagged1 is the pathological link between Wnt and Notch pathways in colorectal cancer. Proc Natl Acad Sci USA, 2009. 106(15): p. 6315-20.
7. Kidd. S. and T. Lieber, Furin cleavage is not a requirement for *Drosophila* Notch function. Mechanisms of development, 2002. 115(1): p. 41-51.
8. De Strooper, B., et al., A presenilin-1-dependent γ-secretase-like protease mediates release of Notch intracellular domain. 1999. 398: p. 518.
9. Struhl. G. and I. Greenwald. Presenilin is required for activity and nuclear access of Notch in *Drosophila*. 1999.398: p. 522.
10. van Es. J. H., et al., Notch/γ-secretase inhibition turns proliferative cells in intestinal crypts and adenomas into goblet cells. Nature, 2005. 435: p. 959.
11. Wu. Y., et al., Therapeutic antibody targeting of individual Notch receptors. Nature, 2010. 464: p. 1052.
12. Riccio, O., et al., Loss of intestinal crypt progenitor cells owing to inactivation of both Notch1 and Notch2 is accompanied by derepression of CDK inhibitors p27Kip1 and p57Kip2. EMBO Rep, 2008. 9(4): p. 377-83.
13. Moellering, R. E., et al., Direct inhibition of the NOTCH transcription factor complex. 2009. 462: p. 182.
14. Astudillo, L., et al., The Small Molecule IMR-1 Inhibits the Notch Transcriptional Activation Complex to Suppress Tumorigenesis. Cancer Research, 2016. 76(12): p. 3593.
15. Luca. V. C., et al., Structural biology. Structural basis for Notch1 engagement of Delta-like 4. Science, 2015. 347 (6224): p. 847-53.
16. Luca. V. C., et al., Notch-Jagged complex structure implicates a catch bond in tuning ligand sensitivity. Science, 2017. 355(6331): p. 1320-1324.
17. Falk. R., et al., Generation of anti-Notch antibodies and their application in blocking Notch signalling in neural stem cells. Methods, 2012. 58(1): p. 69-78.
18. Ridgway. J., et al., Inhibition of D14 signalling inhibits tumour growth by deregulating angiogenesis. Nature, 2006.444: p. 1083.
19. Yan, M., et al., Chronic DLL4 blockade induces vascular neoplasms. Nature, 2010. 463: p. E6.
20. Couch. J. A., et al., Balancing Efficacy and Safety of an Anti-DLL4 Antibody through Pharmacokinetic Modulation. Clinical Cancer Research, 2016. 22(6): p. 1469.
21. Wu, Y., et al., Therapeutic antibody targeting of individual Notch receptors. Nature. 2010. 464(7291): p. 1052-7.
22. Dai, Y., et al., Silencing of Jagged1 inhibits cell growth and invasion in colorectal cancer. Cell Death &Amp; Disease. 2014.5: p. e1170.
23. Jundt. F., et al., Activated Notch1 signaling promotes tumor cell proliferation and survival in Hodgkin and anaplastic large cell lymphoma. Blood, 2002. 99(9): p. 3398-403.
24. Funahashi, Y., et al., A Notch1 ectodomain construct inhibits endothelial Notch signaling, tumor growth, and angiogenesis. Cancer Research, 2008. 68(12): p. 4727-4735.
25. Small. D., et al., Soluble jagged 1 represses the function of its transmembrane form to induce the formation of the Src-dependent chord-like phenotype. Journal of Biological Chemistry, 2001. 276(34): p. 32022-32030.

What is claimed is:

1. A synthetic peptide having a sequence $Z_1$-CLDQIGEFQCI-Z, wherein:
   $Z_1$ is selected from F, I, L, W and Y;
   Z is a sequence of up to 5 amino acids selected from D, E, G, M and P (SEQ ID NO: 41), or a sequence of up to 5 amino acids beginning with C followed by at least one amino acid selected from M, P, D, E and G (SEQ ID NO: 42).

2. The synthetic peptide of claim 1, wherein said sequence is selected from the group consisting of $N1_{T466L}$ (SEQ ID NO: 30), $N102_{M479D}$ (SEQ ID NO: 33), $N102_{M479E}$ (SEQ ID NO: 34), $N102_{T466L-M479E}$ (SEQ ID NO: 36), $N102_{T466W-M479E}$ (SEQ ID NO: 37), $N102_{T46W-M479E}$ (SEQ ID NO: 38), $N102_{T466F-M479E}$ (SEQ ID NO: 39), and $N102_{T466Y-M479E}$ (SEQ ID NO: 40).

3. The synthetic peptide of claim 1, wherein said sequence is $Z_1$-CLDQIGEFQCIC-$Z_2$, wherein $Z_2$ is a negatively charged amino acid (SEQ ID NO: 43).

4. The synthetic peptide of claim 1, having an affinity to the MNNL domain of Jag1.

5. A composition, comprising the synthetic peptide of claim 1.

6. The composition of claim 5, wherein said composition further comprises fucose and/or an anti-cancer drug.

7. The composition of claim 6, wherein said anti-cancer drug is selected from the group consisting of topotecan, 5-fluorouracil, capecitabine, irinotecan, oxaliplatin, doxorubicin, paclitaxel, carmustine, Bevacizumab, lomustine and temozolomide.

8. A method for treating a subject with a disease responsive to Jag1-Notch1 signaling inhibition, comprising administering an effective amount of the synthetic peptide of claim 1 to said subject, wherein said disease is selected from the group consisting of lymphoma, colorectal cancer and glioblastoma.

9. The method of claim 8, further comprising steps of co-administering fucose and/or an anti-cancer drug.

10. The method of claim 9, wherein said anti-cancer drug is selected from the group consisting of topotecan, 5-fluorouracil, capecitabine, irinotecan, oxaliplatin, doxorubicin, paclitaxel, carmustine, Bevacizumab, lomustine and tomozolomide.

11. A method for disrupting Jag1-Notch1 signaling between a mammalian signal-sending cell and a mammalian signal-receiving cell, comprising contacting said mammalian signal-sending cell with the synthetic peptide of claim 1.

12. The method of claim 11, wherein said method further comprises co-administering fucose.

13. The method of claim 11, wherein said synthetic peptide contacts Jag1 of said mammalian signal-sending cell.

14. The method of claim 11, wherein said cell is a tumor cell.

15. The method of claim 11, wherein said tumor cell is from a tumor selected from the group consisting of lymphoma, glioblastoma and colorectal cancer.

* * * * *

UNITED STATES PATENT AND TRADEMARK OFFICE
CERTIFICATE OF CORRECTION

Page 1 of 2

PATENT NO. : 11,117,932 B2
APPLICATION NO. : 17/261573
DATED : September 14, 2021
INVENTOR(S) : Xuezhen Zhu et al.

It is certified that error appears in the above-identified patent and that said Letters Patent is hereby corrected as shown below:

On the Title Page

Item (72) Inventors: "Yu-Wai Chen" should read --Yu Wai Chen--.

In the Specification

Column 1, Line 18: "DLLL" should read --DLL1--;

Column 2, Line 33: "Notch" should read --Notch1--;

Column 3, Line 36: "Notch" should read --Notch1--;

Column 3, Line 42: "Notch" should read --Notch1--;

Column 3, Line 45: "477" should read --I477--;

Columns 5-6, Table 1, Column 2, Row 4: "CLKEYQSRVTAGCPCSF" should read --CLKEYQSRVTAGGPCSF--;

Columns 5-6, Table 1, Column 2, Row 5: "ESENWPRSY" should read --FSFAWPRSY--;

Columns 5-6, Table 1, Column 2, Row 7: "CDDYYYGEGCN" should read --CDDYYYGFGCN--;

Columns 5-6, Table 1, Column 2, Row 10: "CPHGRTGILLC" should read --CPHGRTGLLC--;

Column 6, Line 55: "DLL-induced" should read --DLL1-induced--;

Column 7, Line 54: "N1$_{T466L}$" should read --N1$_{T466}$--;

Column 8, Line 14: "S-M1-80" should read --S1-M1-80--;

Signed and Sealed this
Twenty-fifth Day of January, 2022

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 11,117,932 B2

Column 8, Line 32: "$N102_{T466W-479E}$" should read --$N102_{T466W-M479E}$--;

Column 8, Line 36: "47.3 t 3.1" should read --47.3 ± 3.1--;

Column 8, Line 38: "$N1_{T46L}$" should read --$N1_{T466L}$--;

Column 8, Line 55: "S-M1-80" should read --S1-M1-80--;

Columns 9-10, Table 2, Column 2, Row 2: Delete "Topotecan";

Columns 9-10, Table 2, Column 2, Row 3: Delete "DAPT";

Columns 9-10, Table 2, Column 2, Row 4: Insert --Topotecan--;

Columns 9-10, Table 2, Column 2, Row 5: Insert --DAPT--;

Columns 11-12, Table 2, Column 2, Row 2: Delete "Topotecan";

Columns 11-12, Table 2, Column 2, Row 3: Delete "DAPT"; and

Column 13, Line 21: "CHO-DLL" should read --CHO-DLL1--.

In the Claims

Column 31, Line 39, Claim 2: "$N102_{T466W-M479E}$" should read --$N102_{T466I-M479E}$--;

Column 31, Line 39, Claim 2: "$N102_{T46W-M479E}$" should read --$N102_{T466W-M479E}$--;

Column 32, Line 49, Claim 14: "said cell" should read --said mammalian signal-sending cell--; and Column 32, Line 52, Claim 15: "claim 11" should read --claim 14--.

SEQUENCE LISTING

```
<160> NUMBER OF SEQ ID NOS: 43

<210> SEQ ID NO 1
<211> LENGTH: 17
<212> TYPE: PRT
<213> ORGANISM: Artificial Sequence
<220> FEATURE:
<223> OTHER INFORMATION: Peptide designed from Jag1

<400> SEQUENCE: 1

Cys Leu Lys Glu Tyr Gln Ser Arg Val Thr Ala Gly Gly Pro Cys Ser
1               5                   10                  15

Phe

<210> SEQ ID NO 2
<211> LENGTH: 9
<212> TYPE: PRT
<213> ORGANISM: Artificial Sequence
<220> FEATURE:
<223> OTHER INFORMATION: Peptide designed from Jag1

<400> SEQUENCE: 2

Phe Ser Phe Ala Trp Pro Arg Ser Tyr
1               5

<210> SEQ ID NO 3
<211> LENGTH: 14
<212> TYPE: PRT
<213> ORGANISM: Artificial Sequence
<220> FEATURE:
<223> OTHER INFORMATION: Peptide designed from Jag1

<400> SEQUENCE: 3
```

```
Phe Cys Arg Pro Arg Asp Asp Phe Phe Gly His Tyr Ala Cys
1               5                  10

<210> SEQ ID NO 4
<211> LENGTH: 11
<212> TYPE: PRT
<213> ORGANISM: Artificial Sequence
<220> FEATURE:
<223> OTHER INFORMATION: Peptide designed from Jag1

<400> SEQUENCE: 4

Cys Asp Asp Tyr Tyr Tyr Gly Phe Gly Cys Asn
1               5                  10

<210> SEQ ID NO 5
<211> LENGTH: 10
<212> TYPE: PRT
<213> ORGANISM: Artificial Sequence
<220> FEATURE:
<223> OTHER INFORMATION: Peptide designed from Jag1

<400> SEQUENCE: 5

Cys Gln Tyr Gly Trp Gln Gly Leu Tyr Cys
1               5                  10

<210> SEQ ID NO 6
<211> LENGTH: 10
<212> TYPE: PRT
<213> ORGANISM: Artificial Sequence
<220> FEATURE:
<223> OTHER INFORMATION: Peptide designed from Jag1

<400> SEQUENCE: 6

Cys Glu Thr Asn Trp Gly Gly Gln Leu Cys
1               5                  10

<210> SEQ ID NO 7
<211> LENGTH: 9
<212> TYPE: PRT
<213> ORGANISM: Artificial Sequence
<220> FEATURE:
<223> OTHER INFORMATION: Peptide designed from Jag1

<400> SEQUENCE: 7

Tyr Cys Asp Lys Cys Ile Pro His Pro
1               5

<210> SEQ ID NO 8
<211> LENGTH: 5
<212> TYPE: PRT
<213> ORGANISM: Artificial Sequence
<220> FEATURE:
<223> OTHER INFORMATION: Peptide designed from Jag1

<400> SEQUENCE: 8

Asp Leu Asn Tyr Cys
1               5

<210> SEQ ID NO 9
<211> LENGTH: 11
<212> TYPE: PRT
<213> ORGANISM: Artificial Sequence
<220> FEATURE:
<223> OTHER INFORMATION: Peptide designed from Jag1

<400> SEQUENCE: 9
```

```
Cys Ser Asn Thr Gly Pro Asp Lys Tyr Gln Cys
1               5                  10
```

<210> SEQ ID NO 10
<211> LENGTH: 15
<212> TYPE: PRT
<213> ORGANISM: Artificial Sequence
<220> FEATURE:
<223> OTHER INFORMATION: Peptide designed from Notch1

<400> SEQUENCE: 10

```
Cys Leu Asp Gln Ile Gly Glu Phe Gln Cys Ile Cys Met Pro Gly
1               5                  10                  15
```

<210> SEQ ID NO 11
<211> LENGTH: 14
<212> TYPE: PRT
<213> ORGANISM: Artificial Sequence
<220> FEATURE:
<223> OTHER INFORMATION: Peptide designed from Notch1

<400> SEQUENCE: 11

```
Cys Ser Leu Gly Ala Asn Pro Cys Glu His Ala Gly Lys Cys
1               5                  10
```

<210> SEQ ID NO 12
<211> LENGTH: 12
<212> TYPE: PRT
<213> ORGANISM: Artificial Sequence
<220> FEATURE:
<223> OTHER INFORMATION: Peptide designed from Notch1

<400> SEQUENCE: 12

```
Cys Asp Thr Asn Pro Val Asn Gly Lys Ala Ile Cys
1               5                  10
```

<210> SEQ ID NO 13
<211> LENGTH: 10
<212> TYPE: PRT
<213> ORGANISM: Artificial Sequence
<220> FEATURE:
<223> OTHER INFORMATION: Peptide designed from Notch1

<400> SEQUENCE: 13

```
Cys His Asp Arg Val Ala Ser Phe Tyr Cys
1               5                  10
```

<210> SEQ ID NO 14
<211> LENGTH: 10
<212> TYPE: PRT
<213> ORGANISM: Artificial Sequence
<220> FEATURE:
<223> OTHER INFORMATION: Peptide designed from Notch1

<400> SEQUENCE: 14

```
Cys Pro His Gly Arg Thr Gly Leu Leu Cys
1               5                  10
```

<210> SEQ ID NO 15
<211> LENGTH: 10
<212> TYPE: PRT
<213> ORGANISM: Artificial Sequence
<220> FEATURE:
<223> OTHER INFORMATION: Peptide designed from Notch1

<400> SEQUENCE: 15

```
Cys Val Asn Gly Trp Thr Gly Glu Asp Cys
```

```
1               5                   10
```

<210> SEQ ID NO 16
<211> LENGTH: 15
<212> TYPE: PRT
<213> ORGANISM: Artificial Sequence
<220> FEATURE:
<223> OTHER INFORMATION: Peptide designed from Notch1

<400> SEQUENCE: 16

```
Gln Pro Gly Ile Ile Cys Asp Met Gln Phe Leu Gly Cys Cys Glu
1               5                   10                  15
```

<210> SEQ ID NO 17
<211> LENGTH: 14
<212> TYPE: PRT
<213> ORGANISM: Artificial Sequence
<220> FEATURE:
<223> OTHER INFORMATION: Peptide designed from Notch1

<400> SEQUENCE: 17

```
Cys Leu Asp Gln Ile Gly Glu Phe Gln Cys Ile Cys Met Pro
1               5                   10
```

<210> SEQ ID NO 18
<211> LENGTH: 13
<212> TYPE: PRT
<213> ORGANISM: Artificial Sequence
<220> FEATURE:
<223> OTHER INFORMATION: Peptide designed from Notch1

<400> SEQUENCE: 18

```
Cys Leu Asp Gln Ile Gly Glu Phe Gln Cys Ile Cys Met
1               5                   10
```

<210> SEQ ID NO 19
<211> LENGTH: 12
<212> TYPE: PRT
<213> ORGANISM: Artificial Sequence
<220> FEATURE:
<223> OTHER INFORMATION: Peptide designed from Notch1

<400> SEQUENCE: 19

```
Cys Leu Asp Gln Ile Gly Glu Phe Gln Cys Ile Cys
1               5                   10
```

<210> SEQ ID NO 20
<211> LENGTH: 11
<212> TYPE: PRT
<213> ORGANISM: Artificial Sequence
<220> FEATURE:
<223> OTHER INFORMATION: Peptide designed from Notch1

<400> SEQUENCE: 20

```
Cys Leu Asp Gln Ile Gly Glu Phe Gln Cys Ile
1               5                   10
```

<210> SEQ ID NO 21
<211> LENGTH: 10
<212> TYPE: PRT
<213> ORGANISM: Artificial Sequence
<220> FEATURE:
<223> OTHER INFORMATION: Peptide designed from Notch1

<400> SEQUENCE: 21

```
Cys Leu Asp Gln Ile Gly Glu Phe Gln Cys
1               5                   10
```

```
<210> SEQ ID NO 22
<211> LENGTH: 9
<212> TYPE: PRT
<213> ORGANISM: Artificial Sequence
<220> FEATURE:
<223> OTHER INFORMATION: Peptide designed from Notch1

<400> SEQUENCE: 22

Cys Leu Asp Gln Ile Gly Glu Phe Gln
1               5

<210> SEQ ID NO 23
<211> LENGTH: 8
<212> TYPE: PRT
<213> ORGANISM: Artificial Sequence
<220> FEATURE:
<223> OTHER INFORMATION: Peptide designed from Notch1

<400> SEQUENCE: 23

Cys Leu Asp Gln Ile Gly Glu Phe
1               5

<210> SEQ ID NO 24
<211> LENGTH: 7
<212> TYPE: PRT
<213> ORGANISM: Artificial Sequence
<220> FEATURE:
<223> OTHER INFORMATION: Peptide designed from Notch1

<400> SEQUENCE: 24

Cys Leu Asp Gln Ile Gly Glu
1               5

<210> SEQ ID NO 25
<211> LENGTH: 6
<212> TYPE: PRT
<213> ORGANISM: Artificial Sequence
<220> FEATURE:
<223> OTHER INFORMATION: Peptide designed from Notch1

<400> SEQUENCE: 25

Cys Leu Asp Gln Ile Gly
1               5

<210> SEQ ID NO 26
<211> LENGTH: 5
<212> TYPE: PRT
<213> ORGANISM: Artificial Sequence
<220> FEATURE:
<223> OTHER INFORMATION: Peptide designed from Notch1

<400> SEQUENCE: 26

Cys Leu Asp Gln Ile
1               5

<210> SEQ ID NO 27
<211> LENGTH: 4
<212> TYPE: PRT
<213> ORGANISM: Artificial Sequence
<220> FEATURE:
<223> OTHER INFORMATION: Peptide designed from Notch1

<400> SEQUENCE: 27

Cys Leu Asp Gln
1
```

<210> SEQ ID NO 28
<211> LENGTH: 11
<212> TYPE: PRT
<213> ORGANISM: Artificial Sequence
<220> FEATURE:
<223> OTHER INFORMATION: Peptide designed from Notch1

<400> SEQUENCE: 28

Ile Gly Glu Phe Gln Cys Ile Cys Met Pro Gly
1               5                   10

<210> SEQ ID NO 29
<211> LENGTH: 16
<212> TYPE: PRT
<213> ORGANISM: Artificial Sequence
<220> FEATURE:
<223> OTHER INFORMATION: Peptide designed from Notch1

<400> SEQUENCE: 29

Thr Cys Leu Asp Gln Ile Gly Glu Phe Gln Cys Ile Cys Met Pro Gly
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: Peptide designed from Notch1

<400> SEQUENCE: 30

Leu Cys Leu Asp Gln Ile Gly Glu Phe Gln Cys Ile Cys Met Pro Gly
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: Peptide designed from Notch1

<400> SEQUENCE: 31

Lys Cys Leu Asp Gln Ile Gly Glu Phe Gln Cys Ile Cys Met Pro Gly
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: Peptide designed from Notch1

<400> SEQUENCE: 32

Gln Cys Leu Asp Gln Ile Gly Glu Phe Gln Cys Ile Cys Met Pro Gly
1               5                   10                  15

<210> SEQ ID NO 33
<211> LENGTH: 13
<212> TYPE: PRT
<213> ORGANISM: Artificial Sequence
<220> FEATURE:
<223> OTHER INFORMATION: Peptide designed from Notch1

<400> SEQUENCE: 33

Cys Leu Asp Gln Ile Gly Glu Phe Gln Cys Ile Cys Asp
1               5                   10

```
<210> SEQ ID NO 34
<211> LENGTH: 13
<212> TYPE: PRT
<213> ORGANISM: Artificial Sequence
<220> FEATURE:
<223> OTHER INFORMATION: Peptide designed from Notch1

<400> SEQUENCE: 34

Cys Leu Asp Gln Ile Gly Glu Phe Gln Cys Ile Cys Glu
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Peptide designed from Notch1

<400> SEQUENCE: 35

Cys Leu Asp Gln Trp Gly Glu Phe Gln Cys Ile Cys Met
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Peptide designed from Notch1

<400> SEQUENCE: 36

Leu Cys Leu Asp Gln Ile Gly Glu Phe Gln Cys Ile Cys Glu
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Peptide designed from Notch1

<400> SEQUENCE: 37

Ile Cys Leu Asp Gln Ile Gly Glu Phe Gln Cys Ile Cys Glu
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Peptide designed from Notch1

<400> SEQUENCE: 38

Trp Cys Leu Asp Gln Ile Gly Glu Phe Gln Cys Ile Cys Glu
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Peptide designed from Notch1

<400> SEQUENCE: 39

Phe Cys Leu Asp Gln Ile Gly Glu Phe Gln Cys Ile Cys Glu
1               5                   10

<210> SEQ ID NO 40
```

```
<211> LENGTH: 14
<212> TYPE: PRT
<213> ORGANISM: Artificial Sequence
<220> FEATURE:
<223> OTHER INFORMATION: Peptide designed from Notch1

<400> SEQUENCE: 40

Tyr Cys Leu Asp Gln Ile Gly Glu Phe Gln Cys Ile Cys Glu
1               5                   10

<210> SEQ ID NO 41
<211> LENGTH: 17
<212> TYPE: PRT
<213> ORGANISM: Artificial Sequence
<220> FEATURE:
<223> OTHER INFORMATION: Peptide for Jag1-Notch1 Inhibition
<220> FEATURE:
<221> NAME/KEY: MISC_FEATURE
<222> LOCATION: (1)..(1)
<223> OTHER INFORMATION: Phe, Ile, Leu, Trp, Tyr or absent
<220> FEATURE:
<221> NAME/KEY: MISC_FEATURE
<222> LOCATION: (13)..(13)
<223> OTHER INFORMATION: Asp, Glu, Gly, Met, Pro or absent
<220> FEATURE:
<221> NAME/KEY: MISC_FEATURE
<222> LOCATION: (14)..(14)
<223> OTHER INFORMATION: Asp, Glu, Gly, Met, Pro or absent
<220> FEATURE:
<221> NAME/KEY: MISC_FEATURE
<222> LOCATION: (15)..(15)
<223> OTHER INFORMATION: Asp, Glu, Gly, Met, Pro or absent
<220> FEATURE:
<221> NAME/KEY: MISC_FEATURE
<222> LOCATION: (16)..(16)
<223> OTHER INFORMATION: Asp, Glu, Gly, Met, Pro or absent
<220> FEATURE:
<221> NAME/KEY: MISC_FEATURE
<222> LOCATION: (17)..(17)
<223> OTHER INFORMATION: Asp, Glu, Gly, Met, Pro or absent

<400> SEQUENCE: 41

Xaa Cys Leu Asp Gln Ile Gly Glu Phe Gln Cys Ile Xaa Xaa Xaa Xaa
1               5                   10                  15

Xaa

<210> SEQ ID NO 42
<211> LENGTH: 17
<212> TYPE: PRT
<213> ORGANISM: Artificial Sequence
<220> FEATURE:
<223> OTHER INFORMATION: Peptide for Jag1-Notch1 Inhibition
<220> FEATURE:
<221> NAME/KEY: MISC_FEATURE
<222> LOCATION: (1)..(1)
<223> OTHER INFORMATION: Phe, Ile, Leu, Trp, Tyr or absent
<220> FEATURE:
<221> NAME/KEY: MISC_FEATURE
<222> LOCATION: (14)..(14)
<223> OTHER INFORMATION: Asp, Glu, Gly, Met or Pro
<220> FEATURE:
<221> NAME/KEY: MISC_FEATURE
<222> LOCATION: (15)..(15)
<223> OTHER INFORMATION: Asp, Glu, Gly, Met, Pro or absent
<220> FEATURE:
<221> NAME/KEY: MISC_FEATURE
<222> LOCATION: (16)..(16)
<223> OTHER INFORMATION: Asp, Glu, Gly, Met, Pro or absent
<220> FEATURE:
<221> NAME/KEY: MISC_FEATURE
<222> LOCATION: (17)..(17)
<223> OTHER INFORMATION: Asp, Glu, Gly, Met, Pro or absent

<400> SEQUENCE: 42
```

```
Xaa Cys Leu Asp Gln Ile Gly Glu Phe Gln Cys Ile Cys Xaa Xaa Xaa
1               5                   10                  15

Xaa

<210> SEQ ID NO 43
<211> LENGTH: 14
<212> TYPE: PRT
<213> ORGANISM: Artificial Sequence
<220> FEATURE:
<223> OTHER INFORMATION: Peptide for Jag1-Notch1 Inhibition
<220> FEATURE:
<221> NAME/KEY: MISC_FEATURE
<222> LOCATION: (1)..(1)
<223> OTHER INFORMATION: Phe, Ile, Leu, Trp, Tyr or absent
<220> FEATURE:
<221> NAME/KEY: MISC_FEATURE
<222> LOCATION: (14)..(14)
<223> OTHER INFORMATION: Asp or Glu

<400> SEQUENCE: 43

Xaa Cys Leu Asp Gln Ile Gly Glu Phe Gln Cys Ile Cys Xaa
1               5                   10
```